(12) United States Patent
Edgren et al.

(10) Patent No.: US 8,084,059 B2
(45) Date of Patent: Dec. 27, 2011

(54) ANTIDEPRESSANT DOSAGE FORM

(75) Inventors: David Emil Edgren, El Granada, CA (US); Gurdish Kaur Bhatti, Fremont, CA (US); Zahedeh Hatamkhani, Fremont, CA (US); Patrick S. L. Wong, Palo Alto, CA (US)

(73) Assignee: ALZA Corporation, Palo Alto, CA (US)

( * ) Notice: Subject to any disclaimer, the term of this patent is extended or adjusted under 35 U.S.C. 154(b) by 0 days.

(21) Appl. No.: 11/522,014

(22) Filed: Sep. 15, 2006

(65) Prior Publication Data

US 2007/0009600 A1  Jan. 11, 2007

Related U.S. Application Data

(60) Continuation of application No. 11/315,434, filed on Dec. 22, 2005, now abandoned, and a continuation of application No. 10/696,370, filed on Oct. 28, 2003, now abandoned, which is a continuation of application No. 08/442,292, filed on May 16, 1995, now abandoned, which is a division of application No. 08/068,480, filed on May 27, 1993, now Pat. No. 6,440,457.

(51) Int. Cl.
| | |
|---|---|
| A61K 9/24 | (2006.01) |
| A61K 9/22 | (2006.01) |
| A61K 31/135 | (2006.01) |
| A61K 47/30 | (2006.01) |
| A61K 47/38 | (2006.01) |
| A61K 9/00 | (2006.01) |
| A61P 25/24 | (2006.01) |

(52) U.S. Cl. ........ 424/473; 424/468; 424/472; 514/649; 514/772.3; 514/781; 514/960; 514/964

(58) Field of Classification Search ................ None
See application file for complete search history.

(56) References Cited

U.S. PATENT DOCUMENTS

| | | | |
|---|---|---|---|
| 2,738,303 | A | 3/1956 | Blythe |
| 2,799,241 | A | 7/1957 | Wurster |
| 2,996,431 | A | 8/1961 | Barry |
| 3,133,132 | A | 5/1964 | Loeb et al. |
| 3,139,383 | A | 6/1964 | Neville, Jr. |
| 3,173,876 | A | 3/1965 | Zobrist |
| 3,276,586 | A | 10/1966 | Rosaen |
| 3,541,005 | A | 11/1970 | Strathmann et al. |

(Continued)

FOREIGN PATENT DOCUMENTS

CA  1 169 090 A  6/1984

(Continued)

OTHER PUBLICATIONS

The Merck Index: An Encyclopedia of Chemicals, Drugs, and Biologicals, Fourteenth Edition, Maryadele J. O'Neil, Patricia E. Heckelman, Cherie B. Koch, Kristin J. Roman, Eds. (Merck & Co., Inc., Whitehouse Station, NJ, USA, 2006).*

(Continued)

*Primary Examiner* — Ernst Arnold
*Assistant Examiner* — Christopher R Lea
(74) *Attorney, Agent, or Firm* — RatnerPrestia

(57) ABSTRACT

The invention pertains to a dosage form 10 and to administering an antidepressant medicament 16 for an extended period of time in a rate-known dose.

21 Claims, 1 Drawing Sheet

U.S. PATENT DOCUMENTS

| | | | |
|---|---|---|---|
| 3,541,006 A | 11/1970 | Bixler et al. | |
| 3,546,142 A | 12/1970 | Michaels et al. | |
| 3,598,122 A | 8/1971 | Zaffaroni | |
| 3,598,123 A | 8/1971 | Zaffaroni | |
| 3,625,214 A | 12/1971 | Higuchi | |
| 3,773,919 A | 11/1973 | Boswell et al. | |
| 3,811,444 A | 5/1974 | Heller et al. | |
| 3,845,770 A | 11/1974 | Theeuwes et al. | |
| 3,865,108 A | 2/1975 | Hartop | |
| 3,916,899 A | 11/1975 | Theeuwes et al. | |
| 3,962,414 A | 6/1976 | Michaels | |
| 3,992,518 A | 11/1976 | Chien et al. | |
| 4,029,757 A | 6/1977 | Mlodozeniec et al. | |
| 4,036,228 A | 7/1977 | Theeuwes | |
| 4,063,064 A | 12/1977 | Saunders et al. | |
| 4,066,747 A | 1/1978 | Capozza | |
| 4,070,347 A | 1/1978 | Schmitt | |
| 4,083,949 A | 4/1978 | Benedikt | |
| 4,088,864 A | 5/1978 | Theeuwes et al. | |
| 4,093,709 A | 6/1978 | Choi et al. | |
| 4,111,201 A | 9/1978 | Theeuwes | |
| 4,137,300 A | 1/1979 | Sheth et al. | |
| 4,160,020 A | 7/1979 | Ayer et al. | |
| 4,197,289 A | 4/1980 | Sturzenegger et al. | |
| 4,200,098 A | 4/1980 | Ayer et al. | |
| 4,277,582 A | 7/1981 | Mueller et al. | |
| 4,285,987 A | 8/1981 | Ayer et al. | |
| 4,327,725 A | 5/1982 | Cortese et al. | |
| 4,423,099 A | 12/1983 | Mueller et al. | |
| 4,535,186 A * | 8/1985 | Husbands et al. | 564/336 |
| 4,576,604 A * | 3/1986 | Guittard et al. | 424/473 |
| 4,611,078 A | 9/1986 | Husbands et al. | |
| 4,612,008 A | 9/1986 | Wong et al. | |
| 4,624,848 A | 11/1986 | Lee | |
| 4,624,945 A | 11/1986 | Eckenhoff et al. | |
| 4,721,613 A | 1/1988 | Urquhart et al. | |
| 4,749,576 A | 6/1988 | Lee | |
| 4,761,501 A | 8/1988 | Husbands et al. | |
| 4,765,989 A | 8/1988 | Wong et al. | |
| 4,783,337 A | 11/1988 | Wong et al. | |
| 4,786,503 A | 11/1988 | Edgren et al. | |
| 4,834,985 A | 5/1989 | Elger | |
| 4,842,867 A | 6/1989 | Ayer et al. | |
| 4,853,229 A | 8/1989 | Theeuwes | |
| 4,863,744 A | 9/1989 | Urquhart et al. | |
| 4,946,687 A | 8/1990 | Ayer et al. | |
| 4,948,592 A | 8/1990 | Ayer et al. | |
| 4,950,486 A | 8/1990 | Ayer et al. | |
| 4,966,769 A | 10/1990 | Guittard et al. | |
| 4,980,170 A | 12/1990 | Schneider et al. | |
| 5,017,381 A | 5/1991 | Maruyama et al. | |
| 5,030,456 A | 7/1991 | Ayer et al. | |
| 5,057,321 A * | 10/1991 | Edgren et al. | 424/473 |
| 5,156,850 A | 10/1992 | Wong et al. | |
| 5,178,866 A | 1/1993 | Wright et al. | |
| 5,190,765 A | 3/1993 | Jao et al. | |
| 5,294,770 A | 3/1994 | Riddle et al. | |
| 5,326,570 A | 7/1994 | Rudnic et al. | |
| 5,354,556 A | 10/1994 | Sparks et al. | |
| 5,399,828 A | 3/1995 | Riddle et al. | |
| 5,407,676 A | 4/1995 | Fuisz | |
| 5,413,572 A | 5/1995 | Wong et al. | |
| 5,464,631 A | 11/1995 | Hoover et al. | |
| 5,512,593 A | 4/1996 | Dante | |
| 5,513,293 A | 4/1996 | Holland et al. | |
| 5,516,527 A | 5/1996 | Curatolo | |
| 5,613,958 A | 3/1997 | Kochinke et al. | |
| 5,707,663 A | 1/1998 | Ayer et al. | |
| 5,718,700 A | 2/1998 | Edgren et al. | |
| 5,792,471 A | 8/1998 | Curatolo | |
| 5,837,284 A | 11/1998 | Mehta et al. | |
| 5,874,090 A | 2/1999 | Baker et al. | |
| 5,916,923 A | 6/1999 | Rudolph et al. | |
| 6,022,562 A | 2/2000 | Autant et al. | |
| 6,274,171 B1 * | 8/2001 | Sherman et al. | 424/461 |
| 6,358,527 B1 | 3/2002 | Gilis et al. | |
| 6,440,457 B1 * | 8/2002 | Edgren et al. | 424/468 |
| 6,503,942 B2 | 1/2003 | Yardley et al. | |
| 6,555,586 B2 | 4/2003 | Rudolph et al. | |
| 6,572,890 B2 | 6/2003 | Faour et al. | |
| 6,919,373 B1 | 7/2005 | Lam | |

FOREIGN PATENT DOCUMENTS

| | | |
|---|---|---|
| DE | 2 254 043 | 5/1974 |
| EP | 0 052 510 A2 | 5/1982 |
| EP | 0 068 446 A2 | 5/1983 |
| EP | 0 094 123 A2 | 11/1983 |
| EP | 0 112 669 A2 | 7/1984 |
| EP | 0156592 | 10/1985 |
| EP | 0 164 587 A2 | 12/1985 |
| EP | 0378404 | 7/1990 |
| EP | 0 621 032 A1 | 10/1994 |
| ES | 8704080 | 5/1985 |
| FI | 831096 | 10/1984 |
| FR | 2 588 188 | 4/1987 |
| FR | 2 589 732 | 5/1987 |
| GB | 2 140 687 A | 12/1984 |
| GB | 2 206 046 A | 12/1988 |
| GB | 2 206 047 A | 12/1988 |
| GB | 2 211 091 A | 6/1989 |
| JP | 60-41609 | 3/1985 |
| JP | 60-41609 A | 3/1985 |
| JP | 60-184008 | 9/1985 |
| JP | 60-233012 | 11/1985 |
| JP | 61501511 | 7/1986 |
| JP | 62-77335 | 4/1987 |
| JP | 62-81309 | 4/1987 |
| JP | 62-175424 | 8/1987 |
| JP | 62292733 | 12/1987 |
| JP | 1-157920 | 6/1989 |
| JP | 2229110 | 9/1990 |
| JP | 3-5421 | 1/1991 |
| JP | 3-5421 A | 1/1991 |
| JP | 9-216802 | 8/1997 |
| WO | 8504100 | 9/1985 |
| WO | WO 92/18102 A1 | 10/1992 |
| WO | WO 93/00071 | 1/1993 |
| WO | WO 98/06380 A2 | 2/1998 |
| WO | WO 98/14168 A2 | 4/1998 |
| WO | WO 98/23263 A1 | 6/1998 |

OTHER PUBLICATIONS

Deposition Transcript of Susan Marks, dated Mar. 2, 2004, *Alza Corp.* v. *Mylan Labs*, N.D. West Virginia.

Deposition Transcript of Steven Stone, dated Feb. 19, 2004, *Alza Corp.* v. *Mylan Labs*, N.D. West Virginia.

Deposition Transcript of Patrick S.L. Wong, dated Mar. 10, 2004, *Alza Corp.* v. *Mylan Labs*, N.D. West Virginia.

Deposition Transcript of Seth Fischer, dated Feb. 5, 2005, *Alza Corp.* v. *Mylan Labs*, N.D. West Virginia.

Deposition Transcript of Roger Dmochowski, dated Aug. 19, 2004, *Alza Corp.* v. *Mylan Labs*, N.D. West Virginia.

Deposition Transcript of Michael Chancellor, dated Apr. 1, 2005, *Alza Corp.* v. *Mylan Labs*, N.D. West Virginia.

Deposition Transcript of Douglas Deforge, dated Apr. 23, 2004, *Alza Corp.* v. *Mylan Labs*, N.D. West Virginia.

Deposition Transcript of Michael Desjardin, dated May 13, 2004, *Alza Corp.* v. *Mylan Labs*, N.D. West Virginia.

Deposition Transcript of Fernando Gumucio, dated Mar. 16, 2004, *Alza Corp.* v. *Mylan Labs*, N.D. West Virginia.

Deposition Transcript of George Guittard, dated Feb. 10, 2004, *Alza Corp.* v. *Mylan Labs*, N.D. West Virginia.

Deposition Transcript of Francisco Jao, dated Feb. 24, 2004, *Alza Corp.* v. *Mylan Labs*, N.D. West Virginia.

Deposition Transcript of David Kidney, dated May 12, 2004, *Alza Corp.* v. *Mylan Labs*, N.D. West Virginia.

Expert Report of Roger Dmochowski, dated May 3, 2004, *Alza Corp.* v. *Mylan Labs*, N.D. West Virginia.

Expert Report of Michael Chancellor, dated Dec. 21, 2004, *Alza Corp.* v. *Mylan Labs*, N.D. West Virginia.

Responsive Expert Report of Nicholas Peppas, dated Jun. 1, 2004, *Alza Corp.* v. *Mylan Labs*, N.D. West Virginia.

Responsive Expert Report of Anthony Lowman, dated Jun. 2, 2004, *Alza Corp.* v. *Mylan Labs*, N.D. West Virginia.

Deposition Transcript of David Edgren, dated Oct. 11, 2007, *Wyeth* v. *Impax Labs, Inc.*, Case No. 06-222 (JJF) with Exhibits (1-347).

Dale E. Wurster, Air-Suspension Technique of Coating Drug Particles, 48 J. Am. Pharmaceutical Ass'n. 451 (1959).

Dale E. Wurster, Preparation of Compressed Tablet Granulations by the Air-Suspension Technique II, 49 J. Am Pharmaceutical Ass'n 82 (1960).

Max Hamilton, Rating Scale for Depression, 23 J. Neurology Neurosurgery and Psychiatry 56 (1960).

P. Grafton, General Principles for Designing with Plastics, in Modern Plastics Encyclopedia 62-71 (Sidney Gross ed., McGraw-Hill, Inc. 1969-1970).

Alvin Felmeister, Ph.D., Powders, in Remington's Pharmaceutical Sciences 1626-1680 (John E. Hoover ed., Mack Publishing Co. 14th ed. 1970) (1926).

Murray E. Jarvik, Drugs for Affective Disorders (Depression and Mania), in The Pharmacological Basis of Therapeutics 181-194 (The Macmillan Co. 4th ed. 1970) (1941).

Robert E. King, Tablets, Capsules and Pills, in Remington's Pharmaceutical Sciences 1649-1680 (John E. Hoovered., Mack Publishing Co. 14th ed. 1970) (1929).

Leonard R. Derogatis et al., The Hopkins Symptom Checklist (HSCL): A Self-Report Symptom Inventory, 19 Behavioral Sci. 1 (1974).

Felix Theeuwes, Elementary Osmotic Pump, 64 J. Pharmaceutical Sci. 1987 (1975).

Stuart A. Montgomery & Marie Asberg, A New Depression Scale Designed to be Sensitive to Change, 134 Brit. J. Psychiatry 382, 382-89 (1979).

William Guy, Ph.D., 047 Bprs Brief Psychiatric Rating Scale, in ECDEU Assessment Manual for Psychopharmacology Revised 158-340 (U.S. Dept. of Health, Education, and Welfare,National Institute of Mental Health, Psychopharmacology Research Branch 1976).

E. Marley & Krystyna M. Wozniak, Clinical and Experimental Aspects of Interactions between Amine Oxidase Inhibitors and Amine Reuptake Inhibitors, and Amine Reuptake Inhibitors, 13 Psychological Med. 735 (1983).

Herman P. Winjnand & Cornelis J. Timmer, Mini-Computer Programs for Bioequivalence Testing of Pharmaceutical Drug Formulations in Two-Way Cross-Over Studies, 17 Computer Programs in Biomedicine 73 (1983).

Charles S. Locke, An Exact Confidence Interval from Untransformed Data for the Ratio of Two Formulation Means, 12 J. Pharmacokinetics and Biopharmaceutics 649 (1984).

J.A. Moyer et al., In vivo Antidepressant Profiles of the Novel Bicyclic Compounds Wy-45,030 and Wy-45,881, 10 Soc. Neuroscience 261 (1984).

J.T. Haskins et al., Inhibition of Nora-Drenergic Neuronal Activity by the Novel Bicyclic Compounds, Wy-45,030 and Wy-45,881, 10 Soc. Neuroscience Abstr. 262 (1984).

J.T. Haskins et al., DMI, Wy-45,030, Wy-45,881 and Ciramadol Inhibit Locus Coeruleus Neuronal Activity, 115 Eur. J. Pharmacology, 139 (1985).

Leslie Z. Benet & Lewis B. Sheiner, Pharmacokinetics: The Dynamics of Drug Absorption, Distribution, and Elimination, in the Pharmacological Basis of Therapeutics (Cont.) 1-10 (MacMillan Publishing Co. 7th ed. 1985) (1941).

Eric A. Muth et al., A Pharmacological Profile of Wy-45,233, The Major Metabolite in Humans of the Novel Bicyclic Antidepressant Candidate, Wy-45,030, 12 Soc. Neuroscience Abstr. 473 (1986).

Eric A. Muth et al., Antidepressant Biochemical Profile of the Novel Bicyclic Compound Wy-45,030, An Ethyl Cyclohexanol Derivative, 35 Biochemical Pharmacology 4493 (1986).

S.F. Sisenwine et al., A Prefatory Investigation of the Metabolic Disposition of Wy-45,030 in Man, 59 Acta Pharmacologica et Toxicolologica 312 (1986).

Donald J. Schuirmann, A Comparison of the Two One-Sided Tests Procedure and the Power Approach for Assessing the Equivalence of Average Bioavailability, 15 J. Pharmacokinetics and Biopharmaceutics 657 (1987).

J. Mendels, M.D., Clinical Experience with Serotonin Reuptake Inhibiting Antidepressants, 48 J. Clinical Psychiatry 26 (1987).

Louis F. Fabre & H. Paul Putnam, An Ascending Single-Dose Tolerance Study of Wy-45,030, a Novel Bicyclic Antidepressant, in Healthy Men, 42 Current Therapeutic Research 901 (1987).

Marie Asberg et al., Psychobiology of Suicide, Impulsivity, and Related Phenomena, in Psychopharmacology: The Third Generation of Progress 655-68 (Herbert Y. Meltzer, M.D. ed., Raven Press 1987).

Wayne Katon, The Epidemiology of Depression in Medidcal Care, in 17 Int'l J. Psychiatry in Med. 93-112 (Daniel P. Schubert, M.D., Ph.D. ed., Baywood Publishing Co., Inc. 1987).

Edward Schweizer, M.D. et al., An Open-Label, Dose-Finding Study of Wy-45,030, a Novel Bicyclic Antidepressant, 24 Psychopharmacology Bull. 195 (1988).

Fred W. Reimherr, M.D. et al., Sertraline, a Selective Inhibitor of Serotonin Uptake, for the Treatment of Outpatients with Major Depressive Disorder, 24 Psychopharmacology Bull. 200 (1988).

Harold L. Goldberg, M.D. & Richard Finnerty, Ph.D., An Open-Label, Variable-Dose Study of Wy-45,030 (Venlafexine) in Depressed Outpatients, 24 Psychopharmacology Bull. 198 (1988).

The Merck Index 1365 (Susan Budavari et al. eds., Merck & Co. 11th ed. 1989) (1889).

Gary Gerstenblith & Edward G. Lakatta, Disorders of the Heart, in Principles of Geriatric Medicine and Gerontology 466-75 (William R. Hazard, M.D. et al. eds., McGraw-Hill 2d 1990) (1985).

Kim Brosen, Recent Developments in Hepatic Drug Oxidation, Implications for Clinical Pharmacokinetics, 18 Clinical Pharmacokinetics 466 (1990).

Mark A. Longer & Joseph R. Robinson, Sustained-Release Drug Delivery Systems, in Remington's Pharmaceutical Sciences 676-1686 (Mack Printing Co. 18th ed. 1990) (1926).

Ross J. Baldessarini, Drugs and the Treatment of Psychiatric Disorders, in the Pharmacological Basis of Therapeutics 405-414 (Pergamon Press, Inc. 8th ed. 1990).

V. Parker et al., Effect of Age and Sex on the Pharmacokinetics Venlafaxine, 30 J. Clinical Pharmacology 832 (1990).

Arifulla Khan et al, Venlafaxine in Depressed Outpatients, 27 Psychopharmacology Bull. 141 (1991).

Edward Schweizer, M.D. et al., Placebo-Controlled Trial of Venlafaxine for the Treatment of Major Depression, 11 J. Clinical Psychopharmacology 233 (1991).

R. Rudolph et al., Early Clinical Response in Depression to Venlafaxine Hydrochloride, 29 Biological Psychiatry 630S (1991).

Eric A. Muth et al., Biochemical, Neurophysiological and Behavioral Effects of Wy-45,233 and Other Identified Metabolites of the Antidepressant Venlafaxine, 23 Drug Development Research 191 (1991).

Kimberly Christie Burke et al., Comparing Age at Onset of Major Depression and Other Psychiatric Disorders by Birth Cohorts in Five US Community Populations, 48 Archives of General Psychiatry 789 (1991).

Vernon Parker et al., The Potential Pharmacokinetic Interaction between Venlafaxine and Lithium Carbonate, 31 J. Clinical Pharmacology 867 (1991).

B. Saletu et al., Pharmacodynamics of Venlafaxine Evaluated by EEG Brain Mapping, Psychometry and Psychophysiology, 33 Brit. J. Clinical Pharmacology 589 (1992).

C. Paul Wang, The Disposition of Venlafaxine Enantiomers in Dogs, Rats, and Humans Receiving Venlafaxine, 4 Chirality 84 (1992).

Cross-National Collaborative Group, The Changing Rate of Major Depression: Cross-National Comparisons, 268 JAMA 3098 (1992).

G. Magni & D. Hackett, An Open-Label Evaluation of the Long-Term Safety and Clinical Acceptability of Venlafaxine in Depressed Patients, 15 Clinical Neuropharmacology 323B (1992).

J. Tiller et al., Venlafaxine: A Long Term Study, 15 Clinical Neuropharmacology 342B (1992).

J.C. Samuelian et al., A Randomized, Double-Blind Parallel Group Comparison of Venlafaxine and Clomipramine in Outpatients with Major Depression, 15 Clinical Neuropharmacology 324B (1992).

J.D. Guelfi et al., A Randomized, Double-Blind Comparison of Venlafaxine and Placebo in Inpatients with Major Depression and Melancholia, 15 Clinical Neuropharmacology 323B (1992).

Klamerus et al., Introduction of a Composite Parameter to the Pharmacokinetics of Venlafaxine and its Active O-Desmethyl Metabolite, 32 J. Clinical Pharmacology 716 (1992).

L. Nolan & K. O'Malley, Adverse Effects of Antidepressants in the Elderly, 2 Drugs & Aging 450 (1992).

Michael A. Nader & William L. Woolverton, Evaluation of the Discriminative Stimulus Effects of Venlafaxine, a Potential Antidepressant, in Rhesus Monkeys, 25 Drug Development Research 75 (1992).

NIH Consensus Development Panel on Depression in Late Life, Diagnosis and Treatment of Depression in Late Life, 268 JAMA 1018 (1992).

S. Troy et al., Venlafaxine Pharmacokinetics and Pharmacodynamics, 15 Clinical Neuropharmacology 324B (1992).

C. Bolden-Watson & E. Richelson, Blockade by Newly-Developed Antidepressants of Biogenic Amine Uptake into Rat Brain Synaptosomes, 52 Life Sciences 1023 (1993).

G. Gründer et al., Subchronic Antidepressant Treatment with Venlafaxine or Imipramine and Effects on Blood Pressure: Assessment by Automatical 24 Hour Monitoring 26 Pharmacopsychiatry 155 (1993).

H.V. Semlitsch et al., Acute Effects of the Novel Antidepressant Venlafaxine on Cognitive Event-Related Potentials (P300), Eye Blink Rate and Mood in Young Healthy Subjects, 8 Int'l Clinical Psychopharmacology 155 (1993).

Joseph Mendels, M.D. et al., Efficacy and Safety of b.i.d. Doses of Venlafaxine in a Dose-Response Study, 29 Psychopharmacology Bull. 169 (1993).

Lucy S.C. Wan et al., Relationship between Swelling and Drug Release in a Hydrophilic Matrix, 19 Drug Development and Industrial Pharmacy 1201 (1993).

Paul J. Mitchell & Allan Fletcher, Venlafaxine Exhibits Pre-Clinical Antidepressant Activity in the Resident-Intruder Social Interaction Paradigm, 32 Neuropharmacology 1001 (1993).

Richard Entsuah et al., A Low Relapse Rate Confirms the Long Term Efficacy of Venlafaxine in the Treatment of Major Depression, American College of Neuropsychopharmacology Abstracts of Panels and Posters 192 (unpublished Wyeth-Ayerst research abstract) (Dec. 1993).

S.R. Howell et al., Metabolic Disposition of 14C-Venlafaxine in Mouse, Rat, Dog, Rhesus Monkey and Man, 23 Xenobiotica 349 (1993).

Stuart A. Montgomery, M.D., Venlafaxine: A New Dimension in Antidepressant Pharmacology, 54 J. Clinical Psychiatry 119 (1993).

Andrew A. Nierenberg, M.D. et al., Venlafaxine for Treatment-Resistant Unipolar Depression, 14 J. Clinical Psychopharmacology, 419 (1994).

Bernadette Cusack et al., Binding of Antidepressants to Human Brain Receptors: Focus on Newer Generation Compounds, 114 Psychopharmacology 559 (1994).

David R. Hicks et al., A High Performance Liquid Chromatographic Method for the Simultaneous Determination of Venlafaxine and O-Desmethylvenlafaxine in Biological Fluids, 16 Therapeutic Drug Monitoring 100 (1994).

Edward Schweizer, M.D. et al., Comparison of Venlafaxine and Imipramine in the Acute Treatment of Major Depression in Outpatients, 55 J. Clinical Psychiatry 104 (1994).

Lynn A. Cunningham, M.D. et al., A Comparison of Venlafaxine, Trazodone, and Placebo in Major Depression, 14 J. Clinical Psychopharmacology 99 (1994).

G.E. Clerc et al., A Double-Blind Comparison of Venlafaxine and Fluoxetine in Patients Hospitalized for Major Depression and Melancholia, 139 Int'l Clinical Psychopharmacology 139 (1994).

J. Ferguson et al., A Placebo-Controlled Comparative Study of the Effects on Blood Pressure and Antidepressant Efficacy of Venlafaxine and Imipramine, 10 Neuropsychopharmacology 117 (1994).

Ram K. Shrivastava, M.D. et al., Long-term Safety and Clinical Acceptability of Venlafaxine and Imipramine in Outpatients with Major Depression, 14 J. Clinical. Psychopharmacology 322 (1994).

Steven M. Troy, M.S. et al., The Effect of Renal Disease on the Disposition of Venlafaxine, 56 Clinical Pharmacology Therapeutics 14 (1994).

John P. Feighner, M.D., Cardiovascular Safety in Depressed Patients: Focus on Venlafaxine, 56 J. Clinical Psychiatry 574 (1995).

Stephen M. Holliday & Paul Benfield, Venlafaxine: A Review of its Pharmacology and Therapeutic Potential in Depression, 49 Drugs 280 (1995).

Steven M Troy, M.S. et al., The Pharmacokinetics of Venlafaxine when Given in a Twice-Daily Regimen, 35 J. Clinical Pharmacology 404 (1995).

Steven M. Troy, M.S. et al., Pharmacokinetic and Pharmacodynamic Evaluation of the Potential Drug Interaction between Venlafaxine and Diazepam, 35 J. Clinical Pharmacology 410 (1995).

Steven M. Troy, M.S. et al., Pharmacokinetic Interaction between Multiple-Dose Venlafaxine and Single-Dose Lithium, 36 J. Clinical Pharmacology 175 (1996).

The Merck Index 1695 (Susan Budavari et al. eds., Merck & Co., Inc. 12th ed. 1996) (1889).

Lynn A. Cunningham, M.D., Once-Daily Venlafaxine Extended Release (XR) and Venlafaxine Immediate Release (IR) in Outpatients with Major Depression, 9 Annals of Clinical Psychiatry 157 (1997).

Ryan Luan Vu et al., Rapid Determination of Venlafaxine and O-Desmethylvenlafaxine in Human Plasma by High- Performance Liquid Chromatography with Fluorimetric Detection, 703 J. Chromatography B 195 (1997).

Steven M. Troy, M.S. et al., Pharmacokinetics and Effect of Food on the Bioavailability of Orally, Administered Venlafaxine, 37 J. Clinical Pharmacology 954 (1997).

Steven M. Troy et al., Bioavailability of Once-Daily Venlafaxine Extended Release Compared with the Immediate-Release Formulation in Healthy Adult Volunteers, 58 Current Therapeutic Research 492 (1997).

Alain Patat, M.D., et. al. Absolute Bioavailability and Electroencehalograhic Effects of Conventional and Extended-Release Formulations of Venlafaxine in Healthy Subjects, 38 J. Clinical Pharmacology 256 (1998).

Michael E. Thase, M.D., Effects of Venlafaxine on Blood Pressure: A Meta-Analysis of Original Data From 3744 Depressed Patients, 59 J. Clinical Psychiatry 502 (1998).

Parexel, Parexel International Corporation Statistical Report: A Double-Blind, Placebo-Controlled Study of Venlafaxine-ER and Venlafaxine-OROS in Outpatients With Major Depression, Mar. 4, 1998.

Wolfgang Grimm, Extension of the International Conference on Harmonization Tripartite Guideline for Stability Testing of New Drug Substances and Products to Countries of Climatic Zones 111 and IV, 24 Drug Development and Industrial Pharmacy 313 (1998).

Physicians' Desk Reference 3233-3242 (Lory Murray et al. eds., Medical Economics Company, Inc. 54th ed. 2000).

Keri Wellington and Caroline M. Perry, Venlafaxine Extended-Release: A Review of its Use in the Management of Major Depression, 15 CNS Drugs 643 (2001).

Kenneth F. Ilett, et. al., Distribution of venlafaxine and its O-desmethyl metabolite in human milk and their effects in breastfead infants, 53 Br. J. Clinical Pharmacology 17 (2002).

Marianne Gex Fabry, et. al., Steady-state concentration of venlafaxine enantiomers: model-based analysis of between-patient variablility, 58 Eur. J. Clinical Pharmacology 323 (2002).

Drugdex, Venlafaxine: Drugdex Drug Evaluations, Revised Mar. 2003.

Wyeth, Effexor XR, Revised 2003.

Wyeth, Occurrence of Nausea Coincident with Venlafaxine Therapy/ The Occurrence of Dizziness Coincident with Venlafaxine Therapy, Nov. 4, 2003.

Michael E. Thase, M.D. & Diane M.E. Sloan, Pharm. D., Venlafaxine, in the American Psychiatric Textbook of Psychopharmacology 349-360 (Alan F. Schatzberg, M.D. et al. eds., American Psychiatric Publishing, Inc. 3d ed. 2004).

Benson, H., et al., Pharm. Controlled Release, Pharmaceuticals, 17:290-310 (1982).

Chien, Y., Controlled Drug Release From Polymeric Delivery Systems: Biomedical Applications and Physicochemical Principles, Ch. 2, Drug Delivery Systems. pp. 11-83 (1980).

Decoursin, J., The Controlled-Release Oral Drug Delivery Opportunity, Latest Developments in Drug Delivery Systems Conference Proceedings, Drug Delivery Systems, pp. 29-32 (1985).
Domb, A., et al., Biodegradable Polymers as Drug Carrier Systems, Ch. 13, pp. 399-433 (1994).
Duff, G., Drug Delivery Systems to Enhance Therapeutic Efficiency, British J. of Clinical Practice, Supplement 58, pp. 6-10 (1988).
Healey, J., Enteric Coating and Delayed Release, Ch. 7, Drug Delivery to the Gastrointestinal Tract, Ellis Horwood Ltd., John Wiley and Sons, New York, pp. 83-96 (1989).
Hercules, Inc., Sustained Release Matrix Tablet Formulation with Klucel and Natrosol, Hercules Inc., pp. 1-25 (1986).
Jalsenjak, I., In Vitro Release from Microcapsules and Microspheres, Ch. 11, pp. 193-237, Microcapsules and Nanoparticles in Medicine and Pharmacy, CRC Press, Ann Arbor (1992).
Kato, T., Encapsulated Drugs in Targeted Cancer Therapy, Ch. 7, pp. 200-205, 238-239, Controlled Drug Delivery vol. II Clinical Applications, CRC Press (1983).
Lin, Y., et al., Oral Drug Bioavailability—Variations, Limitations, and Control, Ch. 1, pp. 1-64, Controlled Drug Bioavailability, Ch. 1, pp. 1-64, John Wiley and Sons, New York (1984).
Linhardt, R., Biodegradable Polymers for Controlled Release of Drugs, Ch. 2, pp. 53-95, Controlled Release of Drugs Polymers and Aggregate Systems, VCH Publishers (1989).
Michelson, J., Pilot Plant Scale Up Techniques, The Theory and Practice of Industrial Pharmacy, pp. 626-635 (1976).
Patwardhan, S., et al., Microencapsulation, Ch.5, pp. 122-141, Controlled-Release Technology Bioengineering Aspects, John Wiley and Sons, New York (1983).
Robinson, J., Controlled Release Pharm. Systems (1976).
Shin-Etsu Chemical Company LTD, USP HPMC Metolose SR, ShinEtsu Chemical Co. (Jan. 1993).
Tanquary, A., et al., Controlled Delivery of Biological Active Agents, pp. 3-7 (1972).
Stevens, T., Controlled Release Packaging for the 21st Century, 1990.
Entsuah, R., et al., Effectiveness of Venlafaxine Treatment in a Broad Spectrum of Depressed Patients, Poster No. 9, Abstract, 1995.
Kelsey, J. E., Venlafaxine in Social Phobia, Poster No. 43, Abstract, 1995.
Reimherr, F. W., Open Trial of Venlafaxine in Adult Patients with Attention Deficit Hyperactivity Disorder, Poster No. 81, Abstract, 1995.
Adler, L. A., et al., Open Label Trial of Venlafaxine (Effexor) in Attention Deficit Disorder, Poster No. 90, Abstract, 1995.
Khan, A. et al., Venlafaxine in Depressed Geriatric Outpatients: An Open Label Clinical Study, Poster No. 91, Abstract, 1995.
Hornig-Rohan, M. et al., Venlafaxine vs. Stimulant Therapy in Patents with Dual Diagnoses of Attention Deficit Disorder and Depression, Poster No. 92, Abstract, 1995.
Markovitz, P. J. et al., An Open Trial of Venlafaxine in Borderline Personality Disorder, Free Communication Session B, Abstract, 1995.
English Translation of Japanese Office Action of Patent Application No. 501005/95, dated Jul. 17, 2007.
Amendment and Response after Final, filed Apr. 14, 2008, Ex parte reexamination Control No. 90/008,142.
Second Declaration of Donald R. Paul, Ph.D., filed Apr. 14, 2008, Ex parte reexamination Control No. 90/008,142.
Supplemental Declaration of Richard P. Rozek, Ph.D., filed Apr. 14, 2008, Ex parte reexamination Control No. 90/008,142.
Second Declaration of David E. Edgren, filed Apr. 14, 2008, Ex parte reexamination Control No. 90/008,142.
Amendment and Second Response After Final, filed Jun. 12, 2008, Ex parte reexamination Control No. 90/008,142.
Appeal Brief of Alza Corporation, filed Aug. 13, 2008, Ex parte reexamination Control No. 90/008,142.
Amended Appeal Brief of Alza Corporation, filed Jan. 13, 2009, Ex parte reexamination Control No. 90/008,142.
Examiner's Answer, mailed Sep. 30, 2009, Ex parte reexamination Control No. 90/008,142.
Reply Appeal Brief of Alza Corporation, filed Nov. 30, 2009, Ex parte reexamination Control No. 90/008,142.
"Tolerance and Physical Dependence," *Drill's Pharmacology in Medicine*, Chapter 19, part 3, 1965, pp. 277-280.
"Techniques for Rheological Measurements," *Remington's Pharmaceutical Sciences*, 17th Ed., Chapter 22, 1985, pp. 342-345.
Robert E. King et al., "Oral Solid Dosage Forms," *Remington's Pharmaceutical Sciences*, 17th Ed., Chapter 90, 1985, pp. 1603-1632.
Remington, "Water-Soluble Ointment Bases and Components," *Remington's Pharmaceutical Sciences*, 17th Ed., Chapter 68, 1985, pp. 1305-1306
K.W. Leong et al., "Polymeric controlled drug delivery," *Advanced Drug Delivery Reviews*, 1(1987), pp. 199-233.
Daniel J. Safer et al., "Absence of tolerance to the behavorial effects of methylphenidate in hyperactive and inattentive children," *The Journal of Pediatrics*, vol. 115, Dec. 1989, pp. 1003-1008.
Kennerly S. Patrick et al., "The Absorption of Sustained-Release Methylphenidate Formulations Compared to an Immediate-Release Formulation," *Biopharmaceutics & Drug Disposition*, vol. 10, 1989, pp. 165-171.
Robert J. Linhardt, "Biodegradable Polymers for Controlled Release of Drugs," *Controlled Release of Drugs*, Chapter 2, 1989, pp. 53-95.
John W. Hubbard, "Enantioselective Aspects of the Dispositions of *di-threo*-Methylphenidate after the Administration of a Sustained-Release Formulation to Children with Attention Deficit-Hyperactivity Disorder," *Journal of Pharmaceutical Sciences*, vol. 78, No. 11, Nov. 1989, pp. 944-947.
Item 6025, "Methylphenidate," Merck Index, 11th Edition, 1989, pp. 960.
James Swanson et al., "Development of a New One-a-Day Formulation of Methylphenidate for the Treatment of Attention-deficit/Hyperactivity Disorder," *Arch. Gen. Psychiatry*, vol. 60, Feb. 2003, pp. 204-211.
N.B. Modi, et al., "Single- and multiple-dose pharmacokinetics of an oral once-a-day osmotic controlled-released OROS (methylphenidate HCl) formulation," *J. Clin. Pharmacol.*, vol. 40, 2000, pp. 379-388.
Kennerly S. Patrick et al., "Pharmacology of Methylphenidate, Amphetamine Enantiomers and Pemoline in Attention-Deficit Hyperactivity Disorder," *Human Phsychopharmacology*, vol. 12, 1997, pp. 527-546.
S.K. Gupta et al., "Multiple-dose pharmakinetics and pharmacodynamics of OROS and immediate-release amitriptyline hydrochloride formulations," *J. Clin. Pharmacol.*, 1998, vol. 38, pp. 60-67.
A. Richard Enstuah et al., "Effectiveness of Venlafaxine Treatment in a Broad Spectrum of Depressed Patients: A Meta-Analysis," *Psychopharmacology Bulletin*, vol. 31, No. 4, 1995, pp. 759-766.
Jeffrey E. Kelsey, "Venlafaxine in Social Phobia," *Psychopharmacology Bulletin*, vol. 31, No. 4, 1995, pp. 767-771.
Lenard A. Adler et al., Open-Label Trial of Venlafaxine in Adults With Attention Deficit Disorder[1], *Psychopharmacology Bulletin*, vol. 31, No. 4, 1995, pp. 785-788.
Arifulla Khan et al., "Venlafaxine in Depressed Geriatric Outpatients: An Open-Label Clinical " Study , *Psychopharmacology Bulletin*, vol. 31, No. 4, 1995, pp. 753-758.
Paul J. Markovitz et al., "Venlafaxine in the Treatment of Borderline Personality Disorder," *Psychopharmacology Bulletin*, vol. 31, No. 4, 1995, pp. 773-777.
Sustained Release Medications, pp. 114-151 (J. C. Johnson ed. 1980).
Controlled Drug Delivery—Fundamentals and Applications, pp. 1-94 (Robinson and Lee ed. 1987).
C. J. T. Hoes et al., "The Application of Drug-Polymer Conjugates in Chemotherapy," *Drug Carrier Systems*, pp. 57-109 (Roerdink and Kroon ed. 1989).
The Pharmacological Basis of Therapeutics, pp. 72-73 (Goodman and Gilman ed. 1990).
Physician's Desk Reference, pp. 865-866 (45th ed. 1991).
John L. Haslam et al., "An Osmotic Based System for the Controlled Release of Lipoidal Drugs," *Intl. J. of Pharmaceutics*, vol. 69, No. 11, 1991.
Ronald A. Siegel, "Modelling of Controlled Diffusion Through Porous Matrices Using Monte Carlo Methods," *J. Coll. Interf. Sci.*, vol. 109, 1986, pp. 426-440.

S. Weissberg, "Osmometry," *Encyclopedia of Polymer Science & Technology*, vol. 9, 1968, pp. 659-668.

Hedges D., "An Open Trial of Venlafaxine in Adult Patients with Attention Deficit Hyperactivity Disorder," *Psychopharmacology Bulletin*, vol. 31, No. 4, 1995, pp. 779-783.

Robert S. Langer et al., "Medical Application of Controlled Release," CRC Press, Inc., vol. II, 1984, pp. 2-34.

A. Stiehl et al., "Colonic absorption of usodeoxycholic acid in man," MTP Press Limited. 1987, pp. 323-325.

R. Shrivastava et al., A Dose Response Study of Venlafaxine, 10 Neuropsychopharmacology, pp. 2215 (1994).

The Merck Index p. 1365 (Susan Budavari et al. eds, Merck & Co. 11$^{th}$ Ed. 1989).

"CONCERTA* Product Monograph, 2008 Janssen-Ortho Inc. pp. 1-39.

English Translation of Japanese Office Action in Japanese Patent Application No. 501005/95, dated Sep. 7, 2004.

U.S. Appl. No. 60/028,726, filed Sep. 20, 1996.

U.S. Appl. No. 60/030,514, filed Nov. 12, 1996.

U.S. Appl. No. 60/044,121, filed Apr. 22, 1997.

Order Granting Ex Parte Reexamination for Control No. 90/008,142, dated Oct. 5, 2006.

Office Action in Ex Parte Reexamination for Control No. 90/008,142, dated Feb. 16, 2007.

Final Office Action in Ex Parte Reexamination for Control No. 90/008,142, dated Feb. 13, 2008.

Ex Parte Reexamination Advisory Action for Control No. 90/008,142, dated May 8, 2008.

Ex Parte Reexamination Advisory Action for Control No. 90/008,142, dated Jul. 18, 2008.

Office Action dated Apr. 2, 2010, from JP-2007-301927.

Rodney U. Anderson et al., "Once Daily Controlled Versus Immediate Release Oxybutynin Chloride for Urge Urinary Incontinence", The Journal of Urology, vol. 161, pp. 1809-1812, Jun. 1999.

Michael B. Chancellor et al., "A Comparison of the Effects on Saliva Output of Oxybutynin Chloride and Tolterodine Tartrate", Clinical Therapeutics, vol. 23, No. 5, 2001, pp. 753-760.

Owen I. Corrigan et al., "Influence of dissolution medium buffer composition on ketoprofen release from ER products and in vitro-in vivo correlation", Int'l Journal of Pharmaceutics, 2003, pp. 147-154.

John W. Fara, "Colonic drug absorption and metabolism", John Wiley & Sons Ltd., 1989, pp. 103-112.

Pardeep K. Gupta et al., "Oral Controlled-Release Delivery", Marcel Dekker, Inc., 1992, pp. 255-313.

Glenn D. Leesman et al., "Stimulation of Oral Drug Absorption: Gastric Emptying and Gastrointestinal Motility", Marcel Dekker, Inc., 1988, pp. 267-284.

Mark A Longer et al., "Sustained-Release Drug Delivery Systems", Mack Publishing Co., 1985, pp. 1644-1661.

E. Lukkari et al., "Effect of food on the bioavailability of oxybutynin from a controlled release tablet", Springer-Verlag, 1996, pp. 221-223.

Eeva Lukkari et al., "Effect of Time Interval between Food and Drug Ingestion on the Absorption of Oxybutynin from a Controlled-Release Tablet", Pharmacology & Toxicology, vol. 81, No. 1, Jul. 1997, pp. 31-34.

Etsuko Miyamoto et al., "Physico-chemical Properties of Oxybutynin", Analyst, vol. 119, Jul. 1994, pp. 1489-1492.

Noriko Katori et al., "Estimation of Agitation Intensity in the GI Tract in Humans and Dogs Based on in Vitro/in Vivo Correlation", Pharmaceutical Research, vol. 12, No. 2, 1995, pp. 237-243.

Physicans' Desk Reference, 47 Edition, 1993, pp. 1377-1378.

Vasant V. Randade, et al., "Drug Delivery Systems", CRC Press, 1996, pp. 127-173.

N.W. Read et al., "Gastrointestinal Dynamics and Pharmacology for the Optimum Design of Controlled-Release Oral Dosage Forms", CRC Press, Inc., vol. 4, Issue 3, 1987, pp. 221-263.

Thompson G. Robinson et al., "Drugs in focus: 11. Oxybutynin hydrochloride", Prescribers' Journal, vol. 34, No. 1, 1994, pp. 27-30.

Gayatri Sathyan et al., "Effect of OROS© controlled-release delivery on the pharmacokinetics and pharmacodynamics of oxybutynin chloride", Blackwell Science Ltd., vol. 52, No. 4, Oct. 2001, pp. 409-417.

J. Siepmann et al., "A New Model Describing the Swelling and Drug Release Kinetics from Hydroxypropyl Methylcellulose Tablets", Journal of Pharmaceutical Sciences, vol. 88, No. 1, Jan. 1999, pp. 65-72.

J. Siepmann et al., "HPMC-Matrices for Controlled Drug Delivery: A New Model Combining Diffusion, Swelling, and Dissolution Mechanisms and Predicting the Release Kinetics", Pharmaceutical.Research, vol. 16, No. 11, Nov. 1999, pp. 1748-1756.

Jerome P. Skelly et al "In Vitro and in Vivo Testing and Correlation for Oral Controlled/Modified—Release Dosage Forms", Pharmaceutical Research, vol. 7, No. 9, Sep. 1990, pp. 975-982.

F. Theeuwes et al., "Elementary Osmotic Pump for Indomethacin", Journal of Pharmaceutical Sciences, vol. 72, No. 3, Mar. 1983, pp. 253-258.

Eboo Versi et al., "Dry Mouth with Conventional and Controlled-Release Oxybutynin in Urinary Incontinence", Obstetrics & Gynecology, vol. 95, No. 5, May 2000, pp. 718-721.

H.A. Winkler et al., "Treatment of Detrusor Instability with Oxybutynin Rectal Suppositories", International Urogynecology Journal, vol. 9, No. 1, 1998, pp. 100-102.

Y.E. Yarker et al., "Oxybutynin a Review of its Pharmacodynamic and Pharmacokinetic Properties, and its Therapeutic Use in Detrusor Instability", Adis Int'l, vol. 6, No. 3, Mar. 1995, pp. 243-262.

L.X.Yu et al., "Transport approaches to the biopharmaceutical design of oral drug delivery systems: prediction of intestinal absorption", Advanced Drug Delivery Reviews, vol. 19, No. 3, Jun. 12, 1996, pp. 360-376.

B. Abrahamsson et al., "Absorption, Gastrointestinal Transit, and Tablet Erosion of Felodipine Extended-Release (ER) Tablets", Pharmaceutical Research, vol. 10, No. 5, 1993, pp. 709-714.

K.H. Antonin et al., "Oxprenolol absorption in man after single bolus dosing into two segments of the colon compared with that after oral dosing", British Journal of Clinical Pharmacology, vol. 19, 1985, pp. 137S-142S.

Per Artursson, "Epithelial Transport of Drugs in Cell Culture. I: A Model for Studying the Passive Diffusion of Drugs over Intestinal Absorbtive (Caco-2) Cells", Journal of Pharmaceutical Sciences, vol. 79, No. 6, Jun. 1990, pp. 476-482.

Askew, "A Simple Screening Procedure for Imipramine-Like Antidepressant Agents", Life Sciences, No. 10, 1963, pp. 725-730.

Brockmeier et al., "The Absorption of Piretanide from the Gastro-Intestinal Tract is Site-Dependent", European Journal of Clinical Pharmacology, vol. 30, No. 1, 1986, pp. 79-82.

S.T. Chao et al., "Effect of Food of Bioavailability of Pseudoephedrine and Brompheniramine Administered from a Gastrointestinal Therapeutic System", Journal of Pharmaceutical Sciences, vol. 80, No. 5, May 1991, pp. 432-435.

M. Chung et al., "Clinical Pharmacokinetics of Nifedipine Gastrointestinal Therapeutic System a Controlled-Release Formulation of Nifedipine", The American Journal of Medicine, vol. 83, Dec. 21, 1987, pp. 10-14.

S.S. Davis et al., "Relationship between the rate of appearance of oxprenolol in the systemic circulation and the location of an oxprenolol Oros 16/260 drug delivery system within the gastrointestinal tract as determined by scintigraphy", British Journal of Clinical Pharmacology, vol. 26, No. 4, Oct. 1988, pp. 435-443.

C. Lindsay, "Immediate-Release Versus Controlled-Release Formulations: Pharmacokinetics of Newer Antidepressants in Relation to Nausea", Journal of Clinical Psychiatry, vol. 64, Supplement 18, Dec. 23, 2003, pp. 14-19.

C.H. Gleiter et al., "Colonoscopy in the investigation of drug absorption in healthy volunteers", Gastrointestinal Endoscopy, vol. 31, No. 2, 1985, pp. 71-73.

J. Godbillon et al., "Investigation of drug absorption from the gastrointestinal tract of man. III. metoprolol in the colon", British Journal of Clinical Pharmacology, vol. 19, Supplement 2, 1985, pp. 113S-118S.

P. Gruber et al., "Some biological issues in oral, controlled drug delivery", Advanced Drug Delivery Reviews, vol. 1, Issue 1, 1987, pp. 1-18.

Guidelines for the Design and Evaluation of Oral Prolonged Release Dosage Forms, Ministry of Health and Welfare, Mar. 11, 1988.

S. Harder et al., "Ciprofloxacin absorption in different regions of the human gastrointestinal tract. Investigations with the hf-capsule", British Journal of Clinical Pharmacology, vol. 30, No. 1, Jul. 1990 pp. 35-39.

M.J. Jackson, "Drug Transport Across Gastrointestinal Epithelia", Physiology of the Gastrointestinal Tract, Second Edition, vol. 2, 1987, pp. 1597-1621.

P.H. Marathe et al., "Absorption and Presystemic Metabolism of Nefazodone Administered at Different Regions in the Gastrointestinal Tract of Humans", Pharmaceutical Research, vol. 12, No. 11, Nov. 1995, pp. 1716-1721.

M. Marvola et al., "Gastrointestinal Transit and Concomitant Absorption of Verapamil from a Single-Unit Sustained-Release Tablet", Drug Development and Industrial Pharmacy, vol. 13, Nos. 9-11, 1987, pp. 1593-1609.

G. Parker et al., "Withdrawal reactions associated with venlafaxine", Australian and New Zealand Journal of Psychiatry, vol. 32, No. 2, Apr. 1998, pp. 291-294.

F.G.J. Poelma et al., "Intestinal Absorption of Drugs. The Influence of Mixed Micelles on on the Disappearance Kinetics of Drugs from the Small Intestine of the Rat", Journal of Pharmacy & Pharmacology, vol. 43, No. 5, May 1991, pp. 317-324.

D.W. Powell, "Intestinal Water and Electrolyte Transport", Physiology of the Gastrointestinal Tract, Second Edition, vol. 2, 1987, pp. 1267-1305.

R. Raisman et al., "Specific Tricyclic Antidepressant Binding Sites in Rat Brain Characterised by High-Affinity $^3$H-Imipramine Binding", European Journal of Pharmacology, vol. 61, 1980, pp. 373-380.

S.A. Riley et al., "Absorption of polar drugs following caecal instillation in healthy volunteers", Alimentary Pharmacology & Therapeutics, vol. 6, No. 6, Dec. 1992, pp. 701-706.

A. Sandberg et al., "Steady-State Bioavailability and Day-to-Day Variability of a Multiple-Unit (CR/ZOK) and a Single-Unit (OROS) Delivery System of Metoprolol After Once-Daily Dosing", Pharmaceutical Research, vol. 10, No. 1, Jan. 1993, pp. 28-34.

A.H. Staib et al., "Measurement of Theophylline Absorption from Different Regions of the Gastro-Intestinal Tract Using a Remote Controlled Drug Delivery Device", European Journal of Clinical Pharmacology, vol. 30, No. 6, 1986, pp. 691-697.

F. Theeuwes et al., "Osmotic delivery systems for the β-adrenoceptor antagonists metoprolol and oxprenolol: design and evaluation of systems for once-daily administration", British Journal of Clinical Pharmacology, vol. 19, Supplement 2, 1985, pp. 69S-76S.

M. Tomita et al., "Enhancement of Colonic Drug Absorption by the Paracellular Permeation Route", Pharmaceutical Research, vol. 5, No. 6, 1988, pp. 341-346.

A. Kydonieus (editor), "Treatise on Controlled Drug Delivery", Marcel Dekker, Inc., 1992, Chapters 1-5, pp. 1-253.

S.J. Warrington et al., "Comparison of single-dose pharmacokinetic and pharmacodynamic properties of two metoprolol Oros systems with different initial zero-order release rates", British Journal of Clinical Pharmacology, vol. 19, Supplement 2, 1985, pp. 225S-230S.

I.R. Wilding et al., Gastrointestinal Transit and Systemic Absorption of Captopril from a Pulsed-Release Formulation, Pharmaceutical Research, vol. 9, No. 5, 1992, pp. 654-657.

M.F. Williams et al., "Influence of Gastrointestinal Site of Drug Delivery on the Absorption Characteristics of Ranitidine", Pharmaceutical Research, vol. 9, No. 9, 1992, pp. 1190-1194.

C.G. Wilson et al., "Bimodal release of ibuprofen in a sustained-release formulation: a scintigraphic and pharmacokinetic open study in healthy volunteers under different conditions of food intake", International Journal of Pharmaceutics, vol. 50, 1989, pp. 155-161.

M. Pitsiu et al, "A Semiparametric Deconvolution Model to Establish In Vivo-In Vitro Correlation Applied to Oros Oxybutynin", Pharmaceutical Sciences, vol. 90, No. 6, Jun. 2001, pp. 702-712.

Chi L. Li et al., "The use of hypromellose in oral drug delivery", Journal of Pharmacy and Pharmacology, vol. 57, No. 5, May 2005, pp. 533-546.

S.N. Makhija et al., "Once daily sustained release tablets of venlafaxine, a novel antidepressant", European Journal of Pharmaceutics and Biopharmaceutics, vol. 54, 2002, pp. 9-15.

Brockmeier et al., "Absorption of Glibenclamide from Different Sites of the Gastro-Intestinal Tract", European Journal of Clinical Pharmacology, vol. 29, No. 2, 1985, pp. 193-197.

B.E. Ballard et al., "Prolonged-Action Pharmaceuticals", Remington's Phar. Sci., 14$^{th}$ Ed. 1970, pp. 1699-1714.

Maurizio Fava et al., Emergence of Adverse Events Following Discontinuation of Treatment with Extended-Release Venlafaxine, Am J Psychiatry Dec. 1997, pp. 1760-1762.

Benet, L. Z. et al., Pharmacokinetics: The Dynamics of Drug Absorption, Distribution, & Elimination, The Pharmacological Basis of Therapeutics, 3-34 (MacMillan, 7th ed. 1985).

Burke, Kimberly Christie et al., Comparing Age at Onset of Major Depression and Other Psychiatric Disorders by Birth Cohorts in Five US Community Populations, vol. 48 Archives of General Psychiatry 789-795 (1991).

Ferguson, J. et al., A Placebo-Controlled Comparative Study of the Effects on Blood Pressure and Antidepressant Efficacy of Venlafaxine and Imipramine, vol. 10 Neuropsychopharmacology 165S (1994).

Nierenberg, Andrew A. et al., Venlafaxine for Treatment-Resistant Unipolar Depression, 14 J. Clinical Psychopharmacology, 419-423 (1994).

Benet, Leslie Z., Biopharmaceutics as a Basis for the Design of Drug Products, in Drug Design, E.J. Ariens, Ed., 2-35 (1973).

Schuster, O. & Hugemann, B., Course of development of the HF-Capsule—Variations and method-related typical findings, in Drug Absorption at Different Regions of the Human Gastro-Intestinal Tract: Methods of Investigation and Results, N. Rietbrock, et al., eds, pp. 28-38 (1986).

Hirtz, J., Intubation Techniques for the Study of the Absorption of Drugs in Man, in Drug Absorption at Different Regions of the Human Gastro-Intestinal Tract: Methods of Investigation and Results, N. Rietbrock, et al., eds, pp. 28-38 (1986).

Dennis, Michael J., Absorption Processes, in Comprehensive Medicinal Chemistry, Corwin Hansch, ed., pp. 1-20 (1990).

Friend, David R., ed., Oral Colon-Specific Drug Delivery, pp. 1-114 (1992).

Sommers, D., The effects of omeprazole-induced hypochlorhydria on absorption of theophylline from a sustained-release formulation, Eur. J. Clin. Pharm., 43:2,pp. 141-143 (1992).

Vallner, J., et al., A proposed general protocol for testing bioequivalence of controlled-release drug products, Int. J. Pharm., 16, 47 (1983).

Krowczynski, Extended-Release Dosage Forms, Chp. 1-3, 6 (CRC Press, 1987).

Sedman, G., Trial of a sustained release form of amitriptyline (Lentizol) in the treatment of depressive illness, Brit. J. Psychiat. 123, 69 (1973).

Sims, A. C., Trial of a sustained release form of amitriptyline in the treatment of depressive illness, Brit. 3. Psychiat. 120, 65 (1972).

Robinson, J. R. (Ed.), Sustained and Controlled Release Drug Delivery Systems, 1-3, 8 (Marcel Dekker 1978).

Zajecka, J.M., et al., Coexisting major depression and obsessive-compulsive disorder treated with venlafaxine, J. Clin. Psychopharmacol. Apr. 1990; 10(2):152-3.

Yardley, J.P., et al., 2-Phenyl-2-(1-hydroxycycloalkyl)ethylamine derivatives: synthesis and antidepressant activity, J. Med. Chem. Oct. 1990; 33(10):2899-905.

Controlled Release Polymeric formulations 1-317 (D. R. Paul and F.W. Harris, Eds., American Chemical Society, 1976).

Davis, S.S., Assessment of gastrointestinal transit and drug absorption, Novel Drug Delivery and its Therapeutic Application, Ch 9, pp. 89-101 (1989).

Antonin, Karl-Heinz and Peter R. Bieck, Evaluation of the colonic drug absorption in patients with an artificial intestinal stoma and by colonsocopy in normal volunteers Drug Absorption at Different Regions of the Human Gastro-Intestinal Tract: Methods of Investigation and results, N. Reitbrock, et al., eds., 39-52 (1986).

Hirtz, J.. The Absorption Window Fact or Fiction? 5 Pharm. Int. 175-178 (1984).

King, Robert E., Tablets, Capsules and Pills, Remington's Pharmaceutical Sciences 1649-1680 (John E. Hoover ed., Mack Publishing Co. 14th ed. 1970).

The Pharmacological Basis of Therapeutics, by Goodman & Gilman, 4th Ed., (1970) pp. 182.

The Pharmacological Basis of Therapeutics, by Goodman & Gilman, pp. 407 & 411 (8th Ed., 1990).

*Alza Corp.* v. *Wyeth*, E.D. Texas, court docket, Mar. 30, 2007.

*Alza Corp.* v. *Wyeth*, E.D. Texas, Docket Item 1, Mar. 30, 2007.

*Alza Corp.* v. *Wyeth*, E.D. Texas, Docket Item 14, Mar. 30, 2007.

*Alza Corp.* v. *Wyeth*, E.D. Texas, Docket Item 15, Mar. 30, 2007.

*Alza Corp.* v. *Wyeth*, E.D. Texas, Docket Item 25, Mar. 30, 2007.

*Alza Corp.* v. *Wyeth*, E.D. Texas, Docket Item 29, Mar. 30, 2007.

*Alza Corp.* v. *Wyeth*, E.D. Texas, Docket Item 33, Mar. 30, 2007.

*Alza Corp.* v. *Wyeth*, E.D. Texas, Docket Item 34, Mar. 30, 2007.

*Alza Corp.* v. *Wyeth*, E.D. Texas, Docket Item 41, Mar. 30, 2007.

*Alza Corp.* v. *Mylan Labs., Inc.*, 349 F.Supp.2d 1002 (N.D. W.Va. 2004).

*Alza Corp.* v. *Mylan Labs., Inc.*, 391 F.3d 1365 (Fed. Cir. 2004).

*Alza Corp.* v. *Mylan Labs., Inc.*, 388 F.Supp.2d 717 (N.D. W. Va. 2005).

*Alza Corp.* v. *Mylan Labs., Inc.* 464 F.3d 1286 (Fed. Cir. 2006).

File History for , U.S. Appl. No. 08/068,480 (reduced to substantive communications to and from U.S. Patent and Trademark Office, May 27, 1993.

File History for , U.S. Appl. No. 08/442,292, U.S. Appl. No. 08/442,292 (reduced to substantive communications to and from U.S. Patent and Trademark Office, May 14, 1995.

File History for , U.S. Appl. No. 10/696,217, U.S. Appl. No. 10/696,217 (reduced to substantive communications to and from U.S. Patent and Trademark Office, Oct. 28, 2003.

File History for , U.S. Appl. No. 10/696,370, U.S. Appl. No. 10/696,370 (reduced to substantive communications to and from U.S. Patent and Trademark Office, Oct. 28, 2003.

File History for , U.S. Appl. No. 11/315,434, U.S. Appl. No. 11/315,434 (reduced to substantive communications to and from U.S. Patent and Trademark Office, Dec. 22, 2005.

File History for, U.S. Appl. No. 90/008,142 (including exhibits and declarations), Sep. 6, 2006.

Fabre, Louis F. & H. Paul Putnam, *An Ascending Single-Dose Tolerance Study of Wy-45,030, a Novel Bicyclic Antidepressant, in Healthy Men*, 42 Current Therapeutic Research 901 (1987).

Goldberg, Harold L. & Richard Finnerty, Ph.D., *An Open-Label, Variable-Dose Study of Wy-45,030 (Venlafexine) in Depressed Outpatients*, 24 Psychopharmacology Bull. 198 (1988).

Schweizer, Edward et al., *An Open-Label, Dose-Finding Study of Wy45,030, a Novel Bicyclic Antidepressant*, 24 Psychopharmacology Bull. 195 (1988).

Khan, Arifulla et al., *Venlafaxine in Depressed Outpatients*, 27 Psychopharmacology Bull. 141 (1991).

Rudolph, R. et al., *Early Clinical Response in Depression to Venlafaxine Hydrochloride*, 29 Biological Psychiatry 630S (1991).

Schweizer, Edward et al., *Placebo-Controlled Trial of Venlafaxine for the Treatment of Major Depression*, 11 J. Clinical. Psychopharmacology 233 (1991).

Guelfi, J.D. et al., *A Randomized, Double-Blind Comparison of Venlafaxine and Placebo in Inpatients with Major Depression and Melancholia*, 15 Clinical Neuropharmacology 323B (1992).

Tiller, J. et al., *Venlafaxine: A Long Term Study*, 15 Clinical Neuropharmacology 342B (1992).

Samuelian, J.C. et al , *A Randomized Dnuhle-Blind Parallel Group Comparison of Venlafaxine and Clomipramine in Outpatients with Major Depression*; 15 Clinical Neuropharmacology 324B (1992).

Mendels, Joseph et al., *Efficacy and Safety of b.i.d. Doses of Venlafaxine in a Dose-Response Study*, 29 Psychopharmacology Bull. 169 (1993).

Montgomery, Stuart A., *Venlafaxine: A New Dimension in Antidepressant Pharmacology*, 54 J. Clinical Psychiatry 119 (1993).

Sims, A. C., *Trial of a sustained release form of amitriptyline in the treatment of depressive illness*; Brit. J. Psychiat. 120, 65 (1972).

U.S. Patent No. 4,761,501, Husbands, et al., *Substituted Phenylacetamides* (filed May 22, 1985) (issued Aug. 2, 1988).

Longer, Mark A. & Joseph R. Robinson, *Sustained-Release Drug Delivery Systems*, Remington's Pharmaceutical Sciences 1644-1661 (Mack Printing Co. 17th ed. 1985).

Longer, Mark A. & Joseph R. Robinson, *Sustained-Release Drug delivery Systems*, Remington's Pharmaceutical Sciences 1676-1686 (Mack Printing Co. 18th ed. 1990).

U.S. Patent No. 3,598,122, Zaffaroni, *Bandage for Administering Drugs* (filed Apr. 1, 1969) (issued Aug. 10, 1971).

U.S. Patent No. 3,916,899, Theeuwes, et al., *Osmotic Dispensing Device WIth Maximum and Minimum Sizes For The Passageway* (filed Feb. 7, 1974) (issued Nov. 4, 1975).

U.S. Patent No. 4,111,201, Theeuwes, *Osmotic System for Delivering Selected Beneficial Agents Having Varying Degrees of Solubility* (filed Nov. 22, 1976) (issued Sep. 5, 1978).

U.S. Patent No. 4,327,725, Cortese and Theeuwes, *Osmotic Device With Hydrogel Driving Member* (filed Nov. 25, 1980) (issued May 4, 1982).

Alza Lab Notebook 3198—pp. 16, 23, 35, 38-41, 44-48, 50, 55, 120, 131, 141, Mar. 30, 2007.

Alza Lab Notebook 3286—p. 35, Mar. 30, 2007.

U.S. Patent No. 6,440,457, Edgren, et al., *Method of Administering Antidepressant Dosage Form* (filed May 27, 1993) (issued Aug. 27, 2002).

Curricula vitae of Don Paul, Mar. 30, 2007.

U.S. Patent No. 6,440,457, Edgren, et al., *Method of Administering Antidepressant Dosage Form* (filed May 27, 1993) (issued Aug. 27, 2002).

Gupta, Pardeep K. & Robinson, Joseph R., *Oral Controlled Release Delivery Treatise on Controlled Drug Deliyery*, 255-313 Kyodonieus (NY: Marcel Dekker. Inc., 1992).

Montgomery, Stuart A., *Venlafaxine: A New Dimension in Antidepressant Pharmacology*, 54 J. Clinical Psychiatry 119 (1993).

U.S. Patent No. 4,111,201, Theeuwes, *Osmotic System for Delivering Selected Beneficial Agents Having Varying Degrees of Solubility* (filed Nov. 22, 1976) (issued Sep. 5, 1978).

Alza Lab Notebook 3296, p. 24-28, Mar. 30, 2007.

Antonin, Karl-Heinz and Bieck, Peter R., *Evaluation of the colonic drug absorption in patients with an artificial intestinal stoma and by colonsocopy in normal volunteers, Drug Absorption at Different Regions of the Human Gastro-InteStinal Tract: Methods of Investigation and results* (N. Reitbrock, et al., eds., 39, 1986).

Davis, S.S., *Assessment of gastrointestinal transit and drug absorption*, Novel Drug Delivery and its Therapeutic Application, 90 (1989).

Hirtz, J. *The Absorption Window Fact or Fiction?* 5 Pharm. Int. 175 (1984).

U.S. Patent No. 6,274,171, Sherman, *Extended Release Formulation of Venlafaxine Hydrochloride* (filed Jan. 20, 2000) (issued Aug. 14, 2001).

U.S. Food and Drug Administration Effexor XR Label Approved on Feb. 7, 2007.

*Alza Corp.* v. *Wyeth*, (E.D. Tex. Lufkin Div.), Complaint, Mar. 30, 2007.

Adaptive Innovation, Intellectual Property and the Public Interest: How Patent Extension Leads to More, Better and Safer Medicines, Mar. 30, 2007.

Orange Book: Effexor, Effexor XR, Mar. 30, 2007.

Orange Book: Antidepressants, Mar, 30, 2007.

IP Law 360: Wyeth, Teva Strike Deal on Antidepressant Generic, Oct. 19, 2005.

IP Law 360: Wyeth, Impax Head to Court Over Effexor, Apr. 10, 2006.

IP Law 360: Wyeth Continues Battle Over Antidepressant Drug, Apr. 17, 2006.

IP Law 360: J&J Unit Takes on Wyeth's Effexor in Patent Suit, Jul. 27, 2006.

U.S. Patent No. 6,440,457, Edgren, et al., *Method of Administering Antidepressant Dosage Form* (filed May 27, 1993) (issued Aug. 27, 2002).

U.S. Patent No. 4,761;501, Husbands, et al., *Substituted Phenylacetamides* (filed May 22, 1985) (issued Aug. 2, 1988).

USPTO, Online Patent No. Search—6,440,457, Mar. 30, 2007.

USPTO, Online Patent No. Search—6,274,171, Mar. 30, 2007.

USPTO, Online Patent No. Search—6,403,120, Mar. 30, 2007.

USPTO, Online Patent No. Search—6,419,958, Mar. 30, 2007.

Wyeth's Motion to Strike and Motion to Dismiss (*Impax* v. *Wyeth*), Mar. 30, 2007.
Wellington, Keri and Perry, Caroline M., "Venlafaxine Extended-Release: A Review of its Use in the Management of Major Depression", Mar. 30, 2007.
Entsuah Richard and Chita: Rohini, "A Benefit-risk analysis of once-daily venlafaxine extended release (XR) and venlafaxine immediate release (IR) in outpatients with major depression", Mar. 30, 2007.
Cunningham, Lynn A., M.D., "Once-Daily Venlafaxine Extended Release (XE) and Venlafaxine IMrnediate Release (IR) in Outpatients with Major Depression, Venlafaxine XE 208 Study Group", Mar. 30, 2007.
Effexor XR® Prescribing Information, Mar. 30, 2007.
FDA, Center for Drug Evaluation and Research, Label and Approval History, Effexor XR®, Mar. 30, 2007.
Physicians' Desk Reference, 2000—Effexor XR.
FDA, Center for Drug Evaluation and Research, Label and Approval History, Effexor®, Mar. 30, 2007.
Physicians' Desk Reference, 2006 (Electronic Library)—Effexor.
Gelenberg, Alan J., M:D.; "Psychiatric and Somatic Markers of Anxiety: Identification and Pharmacologic Treatment", Mar. 30, 2007.
Wyeth Pharmaceuticals: Excerpt From Canadian Supplemental New Drug Submission (Dec. 1996), Section 3.2.2.2.2, Venlafaxine Administration to Depressed Patients, pp. 25-41.
Comments to Lachman Consultant Services, Inc. Suitability Petition, Mar. 30, 2007.
DeVane C. Lindsay., "Immediate-release versus controlled-release formulations: pharmacokinetics of newer antidepressants in relation to nausea", Mar. 30, 2007.
Patat, Alain, MD, et al. "Absolute Bioavailability and Electroencephalographic Effects of Conventional and Extended-Release Formulations of Venlafxine in Healthy Subjects", Mar. 30, 2007.
Dual-Action Effexor XR®, Fastest Growing in Antidepressant Market; Effexor XR® Stands Out in Helping Patients Become Virtually Symptom Free, Wyeth Pharmaceuticals, Mar. 30, 2007.
Effexor® XR Shown Effective in Treating GAD Symptoms, Biotech Business, Aug. 1, 2000.
Wyeth-Ayerst Receives U.S. Marketing Clearance for New, Once-Daily Effexor® XR, PR Newswire, Oct. 20, 1997.
Rush, A. John and Ryan, Neal D., "Current and Emerging Therapeutics for Depression", Mar. 30, 2007.
About Medications, Effexor XR® (venlafaxine HCL), National Alliance on Mental Illness, Mar. 30, 2007.
Potential Blockbuster Drugs, Forbes.com, Oct. 8, 2003.
Wyeth Reports Earnings Results for the 2006 Third Quarter and First Nine Months, Wyeth, Oct. 19, 2006.
Wyeth 10-K 2002.
Wyeth Annual Review 2005.
MedAdNews, May 1998, May 1999, May 2000, May 2001, May 2002, May 2003, May 2004, May 2005, and Jun. 2006.
The Drug Development and Approval Process, Medicines in Development for Heart Disease and Stroke, 2005, PhRMA.
DiMasi, Joseph A., Hansen, Ronald W., and Grabowski, Henry G. "The Price of Innovation: New Estimates of Drug Development Costs", Mar. 30, 2007.
Grabowski, Henry and Vernon, John "A New Look at the Returns and to Pharmaceutical R&D", Mar. 30, 2007.
Part 202—Presecription Drug Advertising, § 202.1 Prescription-drug advertisements, 21 CFR Ch. 1 (Apr. 1, 2006 Edition).
Wyeth Affirms Venlafaxine HC1 Extended-Release Capsules only Available as Effexor XR (venlafaxine HCl), Wyeth, Aug. 8, 2006.
Effexor XR Patient Brochure, Mar. 30, 2007.
Guayama Inspection Delay Unlikely to Impact Launches, Wyeth Says, The Pink Sheet, Mar. 7, 2007.
Wyeth Struggling to Avoid Depressed Market for Pristiq, The Pink Sheet, Feb. 5, 2007.
Physicians' Desk Reference, 54th Ed. 2000, Effexor XR.
Correspondence, Mar. 30, 2007.
Nov. 18, 1991 Agreement Between Alza and American Home Products.
Wyeth Effexor XR, Mar. 30, 2007.
Venlafaxine Drugdex Drug Evaluations, Mar. 30, 2007.
Letter, Occurrence of Nausea Coincident with Venlafaxine Therapy, Mar. 30, 2007.
American Psychiatric Assoc, Diagnostic and Statistical Manual of Mental Disorders, 4th Ed., DSM-IV, Anxiety Disorders, pp. 393-444 (1994).
American Psychiatric Assoc, Diagnostic and Statistical Manual of Mental Disorders, 4th Ed., DSM-IV, Mood Disorders, pp. 317-391 (1994).
American Psychiatric Assoc, Diagnostic and Statistical Manual of Mental Disorders, 4th Ed., DSM-IV, Use of the Manual, pp. 1-24 (1994).
PDR—Effexor XR Capsules (Wyeth-Ayerst), pp. 1-31, Mar. 30, 2007.
U.S. Appl. No. 10/413,076 file history, Apr. 14, 2003.
U.S. Appl. No. 11/280,908, Nov. 16, 2005.
Health Law 360: Wyeth Sues fourth Drug Maker Over Generic Effexor, Mar. 14, 2007.
U.S. Food and Drug Administration Paxil Label, Mar. 30, 2007.
U.S. Food and Drug Administration Prozac Label, Mar. 30, 2007.
U.S. Food and Drug Administration Zoloft Label, Mar. 30, 2007.
U.S. Food and Drug Administration Celexa label, Mar. 30, 2007.
U.S. Food and Drug Administration Cymbalta label, Mar. 30, 2007.
U.S. Food and Drug Administration Lexapro label, Mar. 30, 2007.
U.S. Food and Drug Administration Paxil CR label, Mar. 30, 2007.
U.S. Appl. No. 11/274,984, Nov. 16, 2005.
U.S. Appl. No. 11/280,121, Nov. 16, 2005.
U.S. Appl. No. 11/280,124, Nov. 16, 2005.
U.S. Appl. No. 11/280,382, Nov. 16, 2005.
U.S. Appl. No. 11/280,485, Nov. 16, 2005.
U.S. Appl. No. 11/280,712, Nov. 16, 2005.
U.S. Appl. No. 11/281,191, Nov. 16, 2005.
Translation of Office Action dated Sep. 5, 2008, from JP-2007-301927.
Translation of pending claims 1-3 from JP-2007-301927, Sep. 5, 2008.
Proprietary Material: Alza Laboratory Notebook 3198, Apr. 5, 2007.
Proprietary Material: Alza Laboratory Notebook 3199, Apr. 5, 2007.
Proprietary Material: Alza Laboratory Notebook 3286, Apr. 5, 2007.
Proprietary Material: Alza Laboratory Notebook 3296, Apr. 5, 2007.
Proprietary Material: Alza Laboratory Notebook 3394, Apr. 5, 2007.
Proprietary Material: Alza Laboratory Notebook 3418, Apr. 5, 2007.
Proprietary Material: Alza Laboratory Notebook 3476, Apr. 5, 2007.
Proprietary Material: Alza Laboratory Notebook 3482, Apr. 5, 2007.
Proprietary Material: Alza Laboratory Notebook 3540, Apr. 5, 2007.
Proprietary Material: Alza Laboratory Notebook 3582, Apr. 5, 2007.
Proprietary Material: Alza Laboratory Notebook 3872, Apr. 5, 2007.
Proprietary Material: Alza Laboratory Notebook 3899, Apr. 5, 2007.
Proprietary Material: Alza Laboratory Notebook 3969, Apr. 5, 2007.
Proprietary Material: Alza Laboratory Notebook 4006, Apr. 5, 2007.
Proprietary Material: Alza Laboratory Notebook 4090, Apr. 5, 2007.
Proprietary Material: Alza Laboratory Notebook 4100, Apr. 5, 2007.
Proprietary Material: Alza Joint Contract Research Report: Project No. 600A, Report No. 11,263 (20 Pages), including handwritten note, and cover memo reflecting contact date of Jul. 16, 1992.
Proprietary Material: Mar. 4, 1998 Alza Joint Contract Research Report: Statistical Report for Wyeth-Ayerst's Study (72 pages) with cover memo reflecting contact date of Apr. 2, 1998.
Proprietary Material: Letter, Dec. 31, 1992 to FDA re Investigational New Drug Application of Venlafaxine Sustained Release (3 pages).
Proprietary Material: Wyeth Internal Correspondence Jun. 21, 1993 re Preliminary Pharmacokinetic Analysis of Venlafaxine SR Studies (16 pages).
Proprietary Material: Wyeth Internal Correspondence Jun. 9, 1994 re Preliminary Pharmacokinetic Analysis of Venlafaxine ER Studies (10 pages) with cover memo reflecting contact date of Jun. 9, 1994.
Proprietary Material: CD, includes on Adove PDF file and three folders containing data obtained by Dr. Richard Rozek; the contents of each folder is described below, Apr. 4, 2007, Folder 1 includes data relied on by Richard Rozek in preparing his Mar. 19, 2007 declaration. Folder 2 includes data reviewed buy not relied on by Richard Rozek in preparing his Mar. 19, 2007 declaration. Folder 3 includes superceded data not relied on by Richard Rozek in preparing his Mar. 19, 2007 declaration.

Proprietary Material: CD, includes two filed containing additional data regarding the antidepressant market, Apr. 4, 2007.

*Wyeth* v. *Anchen Pharmaceuticals, et al.* Civil Minutes—General—Order Re Claim Construction, Feb. 6, 2008.

*Wyeth* v. *Impax Laboratories, Inc.* Claim Construction Order dated Dec. 13, 2007.

*Wyeth* v. *Impax Laboratories, Inc.* Memorandum Opinion dated Dec. 13, 2007.

*Wyeth* v. *Impax Laboratories, Inc.* Declaration of Mary B. Matterer (with Exhibits)—Redacted by Litigants, Not by Applicants, Feb. 6, 2008.

Wyeth's Counterstatement Certifying that Genuine Issues of Material Fact Exist Precluding Grant of Impax's Motion for Summary Judgment of Anticipation and Obviousness—Redacted by Litigants, Not by Applicants, Feb. 6, 2008.

Impax Laboratories, Inc.'s Motion for Summary Judgment of Anticipation and Obviousness—Redacted by Litigants, Not by Applicants, Feb. 6, 2008.

Impax Laboratories, Inc.'s Motion for Summary Judgment of Noninfringement, Lack of Written Description, Lack of Enablement, Misjoinder of Inventors, and Indefiniteness—Redacted by Litigants, Not by Applicants, Feb. 6, 2008.

Wyeth's Counterstatement Certifying That Genuine Issues of Material Fact Exist Precluding Grant of Impax's Motion for Summary Judgment of Non-Infringement, Lack of Written Description, Lack of Enablement, Misjoinder of Inventors, and Indefiniteness—Redacted by Litigants, Not by Applicants, Feb. 6, 2008.

Volume IV of IV (Exhibits 30-67) to the Consolidated Declaration of Karen Jacobs Louden in Support of Wyeth's Counterstatement in Opposition to Impax's Motions for Summary Judgment—Redacted by Litigants, Not by Applicants, Feb. 6, 2008.

Office Action of Nov. 8, 2010, in U.S. Appl. No. 12/820,671.

Board of Patent Appeals and Interferences Decision on Appeal of Dec. 10, 2010, in U.S. Appl. No. 90/008,142.

Board of Patent Appeals and Interferences Record of Oral Hearing of Dec. 15, 2011, in U.S. Appl. No. 90/008,142.

Notice of Intent to Issue Ex Part Reexamination Certificate of Feb. 11, 2011, in U.S. Appl. No. 90/008,142.

Ex Parte Reexamination Certificate No. US 6,440,457 C1 issued May 3, 2011.

Office Action of Dec. 1, 2010, in related Japanese Application No. 2010-173633, with translation.

*Alza Corp.* v. *Andrx Pharm., LLC*, (Fed. Cir. Apr. 26, 2010).

US 6,034,101, 03/2000, Gupta et al. (withdrawn)

* cited by examiner

ANTIDEPRESSANT DOSAGE FORM

CROSS REFERENCE TO RELATED APPLICATIONS

This application is a continuation of U.S. application Ser. No. 10/696,370, filed Oct. 28, 2003, abandoned, and a continuation of U.S. application Ser. No. 11/315,434, filed Dec. 22, 2005, abandoned, each of which is a continuation of U.S. application Ser. No. 8/442,292, filed May 16, 1995, abandoned, which is a divisional application claiming benefit of U.S. application Ser. No. 8/068,480, filed May 27, 1993, which issued as U.S. Pat. No. 6,440,457 on Aug. 27, 2002. U.S. application Ser. Nos. 10/696,370, 11/315,434, and 8/442,292 are incorporated by reference herein in their entirety.

FIELD OF THE INVENTION

This invention pertains to a controlled-release dosage form comprising a compound of the following structural formula:

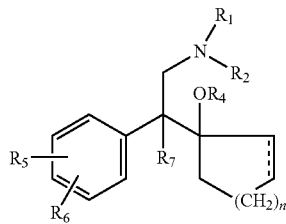

useful for antidepressant therapy. The invention concerns also a method useful for antidepressant therapy by administering the controlled-release dosage form comprising the compound of the formula.

BACKGROUND OF THE INVENTION

The primary goal of drug administration is to provide a therapeutic dose of drug in the body to achieve a desired blood concentration, and then maintain the desired drug blood concentration. The prior art, in attempts to obtain the desired therapeutic effect, often used different dosage forms or programs. One dosage program consists of a single dosing of the drug from a conventional capsule or tablet that produced a rapid rise followed by an immediate decline of the drug blood level versus time. The single dosing does not maintain the drug within a therapeutic range for an extended period of time, but exhibits of a short duration of action due to the inability of the conventional dosage form to provide drug delivery over time.

Another prior art dosing program used to obtain and to achieve drug blood levels consists in administering the drug repetitively using conventional dosage forms at various dosing intervals, as in multiple-dose therapy. In administering a drug according to the multiple-dose therapy, the drug blood level reached and the time required to reach that level depends on the dose and the dosing interval. There are, however, several potential problems inherent in multiple dose therapy. For example, if the dosing interval is not appropriate for the biological half-life of the drug, large peaks and valleys may result in the drug blood levels. Also, the drug blood level may not be within the therapeutic range at sufficiently early times, an important consideration for many disease states. And too, patient noncompliance with the multiple dosing regimen can result in a failure of this approach, especially as a drug in circulation surges to a high each time the drug is administered followed by a decline in drug concentration in the blood and in body compartments. Thus, a graph of drug in circulation following a dosage program of several doses, has an appearance of a series of peaks, which may surpass the toxic threshold. Then, each time the blood levels decreases into valleys, below a critical level needed to achieve a desired therapeutic effect, that effect may not be obtainable in the blood and body. Conventional dosage forms and their mode of operation are discussed in Remington's Pharmaceutical Sciences, 18th Edition, pages 1676 to 1686, (1990), Mack Publishing Co.; The Pharmacological Basis of Therapeutics, 7th Edition, page 7 (1985) published by MacMillian Publishing Co., and in U.S. Pat. Nos. 3,598,122 and 3,598,123 both issued to Zaffaroni.

A critical need exists for a controlled-rate dosage form for administering the drug of the formula:

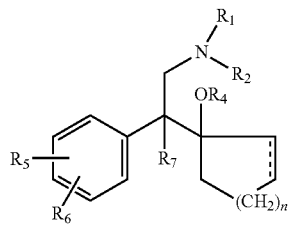

which drug is presently administered in conventional dosage forms including tablets, capsules, elixirs and suspensions. These conventional dosage forms produce the peaks and valleys drug pattern presented above and they do not provide for controlled-rate therapy over an extended period of time. The drug of the formula is dosed twice or thrice a day now because of its elimination half-life of three to five hours. This patern of dosing indicates the need for a controlled-release dosage form that can administer the drug at a controlled rate over an extended time to provide constant therapy and thereby eliminate the need for multiple dosing. The drugs of the structural formula are known in U.S. Pat. Nos. 4,535,186; 4,611,078; and 4,761,501 all issued to Husbands, Yardley and Muth.

The prior art provided controlled-release dosage forms that can continuously over time administer a drug for controlled-rate therapy. For example, in U.S. Pat. No. 4,327,725 issued to Cortese and Theeuwes and in U.S. Pat. Nos. 4,612,008; 4,765,989; and 4,783,337 issued to Wong, Barclay, Deters, and Theeuwes. The dosage forms disclosed in these patents provide a drug at a constant rate for effecting a therapeutic range for preferred therapy. The dosage forms of the patents provide a therapeutic range and avoids delivering the drug in excess in a toxic range with its accompanying side-effects. The dosage forms of the patents in providing a controlled dose in a therapeutic range also avoids delivering the drug in an ineffective dose in an ineffective range.

The dosage forms presented immediately above operate successfully for their intended use and they can deliver many drugs indicated for good therapy. The drugs of the above structural formula, however, possess properties such as a high solubility of 570 mg per ml at a body temperature of 37° C. that can lead to a premature release of the drug from the dosage form. During operation of the dosage forms, the convection motion of the imbibed fluid, and the hydrostatic pressure of the imbibed fluid coupled with the high solubility can result in the premature release of the drugs of the formula.

It is immediately apparent in the light of the above presentation that an urgent need exists for a dosage form endowed with controlled-release delivery for delivering the drugs embraced by the structural formula. The need exists for the dosage form for delivering the drug at a controlled dose in a therapeutic range while simultaneously providing the intended therapy. It will be appreciated by those versed in the dispensing art, that such a dosage form that can administer the drug in a controlled-rate dose over time, would, represent an advancement and a valuable contribution to the art.

OBJECTS OF THE INVENTION

Accordingly, in view of the above presentation, it is an immediate object of this invention to provide a dosage form that possesses controlled-release delivery for providing a dosage form for administering a drug of the structural formula.

Another object of the present invention is to provide a dosage form for administering the drug of the formula in a controlled-rate dose in a therapeutic range over a prolonged period of time.

Another object of the present invention is to provide a dosage form that can deliver the drug of the formula essentially-free of a premature release from the dosage form.

Another object of the present invention is to provide a drug delivery controlled-release system that can deliver a drug for maintaining constant drug levels in the blood thereby functioning as a prolonged release system.

Another object of the present invention is to provide drug delivery sustained-release system that provides slow release of the drug over an extended period of time optionally in a therapeutic range.

Another object of the present invention is to provide a dosage form that substantially reduces and/or substantially eliminates the unwanted influences of a gastrointestinal environment of use and still provides controlled drug administration.

Another object of the present invention is to provide an improvement in a dosage form for administering a drug embraced by the structural formula and its pharmaceutically acceptable salt, wherein the improvement comprises delivering the drug in a controlled-release rate from the dosage form for improved and known therapy.

Another object of the invention is to provide a once-a-day controlled-release dosage form to deliver the drug of the structural formula orally to a patient in need of therapy.

Another object of the invention is to provide a method for administering a drug of the formula by orally administering the drug in a controlled rate dose per unit dose over an extended time to an animal in need of therapy.

Another object of the present invention is to provide a method for administering a drug of the formula in a therapeutic range while simultaneously substantially-avoiding a toxic range and an infective range.

Another object of the present invention is to provide a therapeutic composition comprising a drug of the structural formula blended with a drug-composition forming polymer.

Another object of the invention is to provide a therapeutic composition comprising a member selected from the group consisting of venlafaxine and its pharmaceutically acceptable additional salt and a pharmaceutically acceptable polymer carrier for venlafaxine and its acceptable salts.

Other objects, features, and advantages of the invention will be more apparent to those versed in the dispensing arts from the following detailed specification, taken in conjunction with the drawings and the accompanying claims.

BRIEF DESCRIPTION OF THE DRAWINGS

In the drawing figures, which are not drawn to scale, but are set forth to illustrate various embodiments of the invention, the drawing figures are as follows.

Drawing

Drawing

In the drawing figures, and in the specification, like parts in related figures are identified by like numbers. The terms appearing earlier in the specification and in the description of the drawing figures, as well as embodiments thereof, are further described elsewhere in the disclosure.

DETAILED DESCRIPTION OF THE DRAWINGS

Figure 1:
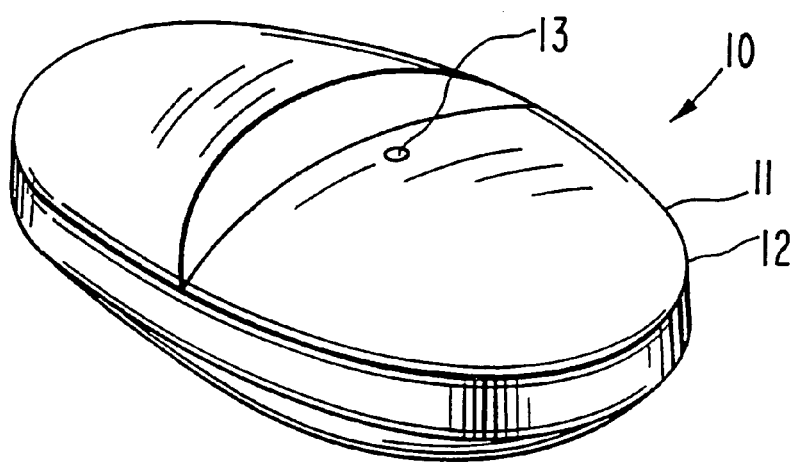
FIG. 1 is a general view of a dosage form provided by the invention, which dosage form is designed and shaped for oral administration, and for a drug delivery in a controlled-rate dose in the gastrointestinal tract.

Turning now to the drawing figures in detail, which drawing figures are examples of dosage forms provided by this invention, and which examples are not to be construed as limiting, one example of a dosage form is seen in drawing FIG. 1. In drawing FIG. 1, a dosage form 10 is seen comprising a body member 11, which body 11 comprises wall 12, that surrounds and forms an internal area, not seen in drawing FIG. 1. Dosage form 10 comprises at least one exit port 13 for connecting the exterior with the interior of dosage form 10.

The dosage form 10 of drawing FIG. 1 illustrates a controlled-release dosage form manufactured as an osmotic dosage form that delivers a drug by osmotic action over an extended period of time. The dosage form comprising controlled-release properties embraced by this invention are successful at maintaining substantially constant drug levels in the blood or in a tissue. The dosage forms within the mode and manner of this invention comprises also sustained-release dosage forms. The sustained-release dosage forms releases the drug and provide drug levels in the blood or target tissue within a therapeutic range over an extended period of time. The invention embraces additionally prolonged release dosage forms. The prolonged release dosage form denotes extended duration of drug delivery action over that achieved by conventional drug delivery.

Figure 2:
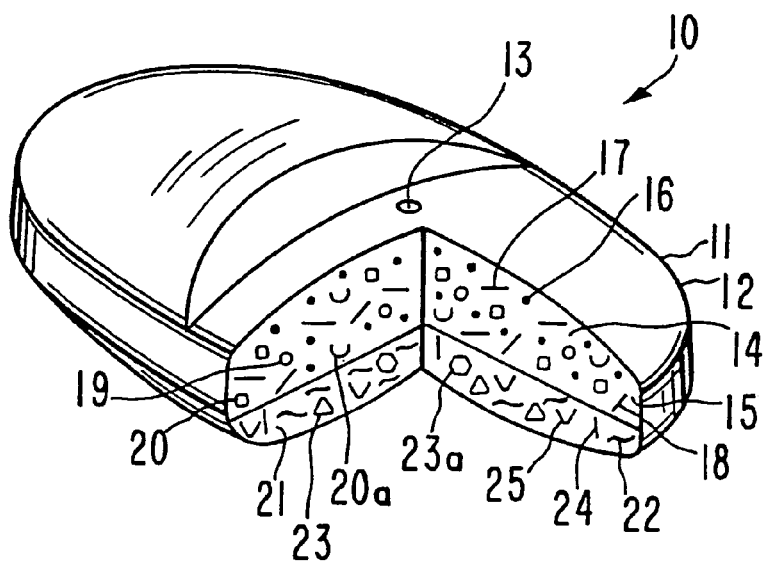
FIG. 2 is an opened view of the dosage form of drawing FIG. 1 for depicting the structure of the dosage form and the composition member contained inside the dosage form; and Drawing

In drawing FIG. 2, dosage form 10 of FIG. 1 is seen in opened section. In drawing FIG. 2, dosage form 10 comprises a body 11, a wall 12 that surrounds and defines an internal compartment 14. In drawing FIG. 2, internal compartment 14 communicates through an exit passageway 13 with the exterior of dosage form 10.

Wall 12 of dosage form 10 comprises totally or in at least a part of a composition that is permeable to the passage of an exterior fluid present in an environment of use, such as aqueous and biological fluids. Wall 12 is formed of nontoxic ingredients, is substantially impermeable to the passage of a drug and other ingredients present in compartment 14. Wall 12 comprises a composition that is substantially inert, that is, wall 12 maintains its physical and chemical integrity during the drug dispensing life of a drug from dosage form 10. The phrase, "maintaining its physical and chemical integrity,"

means wall 12 does not lose its structure and it does not change during the dispensing life of dosage form 10, except for possible leaching of one or more exit 13 passageway formed during operation of dosage form 10 or for leaching a water-soluble flux enhancers blended into wall 12. Wall 12 comprises a material that does not adversely affect an animal, a human or any other components comprising the dosage form. Representative materials for forming wall 12, are in one embodiment, a cellulose ester polymer, a cellulose ether polymer and a cellulose esterether polymer. These cellulosic polymers have a degree of substitution. D.S., on the anhydroglucose unit, from greater than 0 up to 3 inclusive. By degree of substitution is meant the average number of hydroxyl groups originally present on the anhydroglucose unit comprising the cellulose polymer that are replaced by a substituting group. Representative materials include a member selected from the group consisting of cellulose acylate, cellulose diacylate, cellulose triacylate, cellulose acetate, cellulose diacetate, cellulose triacetate, mono-, di- and tricellulose alkanylates, mono-,di-, and tricellulose aroylates, and the like. Exemplary polymers include cellulose acetate having a D.S. up to 1 and an acetyl content up to 21%; cellulose acetate having a D.S. of 1 to 2 and an acetyl content of 21 to 35%; cellulose acetate having a D.S. of 2 to 3 and an acetyl content of 35 to 44.8%, and the like. More specific cellulosic polymers include cellulose propionate having a D.S. of 1.8 and a propyl content of 39.2 to 45% and a hydroxyl content of 2.8 to 5.4%; cellulose acetate butyrate having a D.S. of 1.8, an acetyl content of 13 to 15% and a butyryl content of 34 to 39%; cellulose acetate butyrate having an acetyl content of 2 to 29%, a butyryl content of 17 to 53% and a hydroxyl content of 0.5 to 4.7; cellulose triacylates having a D.S. of 2.9 to 3 such as cellulose trivalerate, cellulose trilaurate, cellulose tripolmitate, cellulose trisuccinate, and cellulose trioctanoate; cellulose diacylates having a D.S. of 2.2 to 2.6 such as cellulose disuccinate, cellulose dipalmitate, cellulose dioctanoate, cellulose dipentanoate, co-esters of cellulose such as cellulose acetate butyrate and cellulose acetate propionate, and the like.

Additional polymers include ethyl cellulose of various degree of etherification with ethoxy content of from 40% to 55%, acetaldehyde dimethyl cellulose acetate, cellulose acetate ethyl carbamate, cellulose acetate methyl carbamate, cellulose acetate diethyl aminoacetate, semipermeable polyamides; semipermeable polyurethanes; semipermeable sulfonated polystyrenes; semipermeable cross-linked selective polymers formed by the coprecipitation of a polyanion and a polycation as disclosed in U.S. Pat Nos. 3,173,876, 3,276,586, 3,541,005; 3,541,006, and 3,546,142; semipermeable polymers as disclosed by Loeb and Sourirajan in U.S. Pat. No. 3,133,132; semipermeable lightly cross-linked polystyrene derivatives, semipermeable cross-linked poly(sodium styrene sulfonate); semipermeable cross-linked poly(vinylbenzyltrime.thyl ammonium chloride); semipermeable polymers exhibiting a fluid permeability of $2.5 \times 10^{-8}$ to $2.5 \times 10^{-4} (cm^2/hr.atm)$ expressed per atmosphere of hydrostatic or osmotic pressure difference across the semipermeable wall. The polymers are known to the art in U.S. Pat. Nos. 3,845,770; 3,916,899; and 4,160,020; and in Handbook of Common Polymers by Scott, J. R. and Roff, W. J., 1971 published by CRC Press, Cleveland, Ohio.

Compartment 14 comprises a drug composition, identified as drug layer 15 which contains drug 16, identified by dots. Drug 16 comprises a drug of the following structural formula:

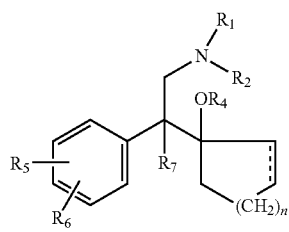

wherein the dotted line represents optional unsaturation or a cycloalkenyl moiety; $R_1$ is a member selected from the group consisting of hydrogen and alkyl of 1 to 6 carbon atoms; $R_2$ is a member selected from the group consisting of hydrogen and alkyl of 1 to 6 carbon atoms; $R_4$ is a member selected from the group consisting of hydrogen, alkyl of 1 to 6 carbon atoms, formyl, and alkanoyl of 2 to 7 carbon atoms; $R_5$ and $R_6$ are independently a member selected from the group consisting of hydrogen, hydroxyl, an alkyl of 1 to 6 carbon atoms, an alkoxy of 1 to 6 carbon atoms, alkanoyloxy of 2 to 7 carbon atoms, nitro, alkylmercapto of 1 to 6 carbon atoms, amino, alkylamino of 1 to 6 carbon atoms in which each alkyl group comprises 1 to 6 carbon atoms, alkanamido of 2 to 7 carbon atoms, halo, and trifluoroethyl, $R_7$ is a member selected from the group consisting of hydrogen and alkyl of 1 to 6 carbons, and n is one of the integers 0, 1, 2, 3, and 4. The formula embraces also the pharmaceutically acceptable addition salts including a member selected from the group consisting of inorganic, organic, hydrochloric, hydrobromic, gluconic, fumaric, maleric, sulfonic, succinic, sulfuric, phosphoric, tartaric, acetic, proponic, citric, oxalic and similar pharmaceutically acceptable addition salts. The compounds are known in U.S. Pat. Nos. 4,535,186; 4,611,078; 4,761,501; and 5,190,765.

The drugs of the structural formula are represented by the drug 1-[2-(dimethylamino)-1-(4-methoxyphenyl)ethyl]cyclohexanol of the structural formula:

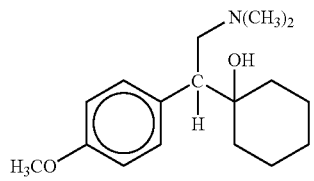

The drug embraced by the formula possesses antidepressant properties. The drug in vitro prevents the neuronal uptake of serotonin, morepinephrine, and dopamine and it does not inhibit monoamine oxidase. The drug antagonizes reserpine-induced hypothermia and potentiates the effects of levodopa, and reduces histamine-induced corticotropin release and induces cyclicadenosine monophosphate subsensitivity after both acute and chronic administration. The drug possesses excellent antidepressant activity in humans. The therapeutic amount of drug 16 in dosage form 10 is 0.5 mg to 750 mg, with individual dosage forms comprising 2, 5, 10, 25, 40, 50, 75, 100, 150, 250, 300, 500, and 600 mg of drug 16 for administering in a single dose or more then one dose over an extended period of 24 hours. The therapeutic properties of the drug embraced by the structural formula are reported in Current Therapeutic Research, Vol. 42, No. 5, pages 901 to 909 (1987).

Composition 15 comprising drug 16 may comprise a drug dispensing carrier and composition formulating member consisting of a member selected from the group consisting of 0 wt % to 25 wt % of a hydroxypropylalkylcellulose where alkyl consists of 1 to 7 carbons selected from the group consisting of methyl, ethyl, isopropyl, butyl, pentyl, and hexyl which cellulose member comprises a 9,000 to 1,250,000 molecular weight and is exemplified by hydroxypropylmethylcelluose, hydroxypropylethylcellulose, hydroxypropylisopropylcellulose, hydroxypropylbutylcellulose and hydroxypropylhexylcellulose represented by dashes 17; a member selected from the group consisting of 0 wt % to 20 wt % hydroxylalkylcellulose where alkyl is 1 to 6 carbons including methyl, ethyl, propyl, butyl, pentyl, and hexyl which cellulose member comprises a 7,500 to 750,000 molecular weight and is exemplified by hydroxymethylcellulose, hydroxyethylcellulose, hydroxypropylcellulose, hydroxyisopropylcellulose and hydroxybutylcellulose as represented by slanted line 18; a member selected from the group consisting of 0 wt % to 35 wt % of a vinyl-polymer having a 3,500 to 750,000 molecular weight represented by poly-n-vinylamide, poly-n-vinlycetamide, poly-n-vinylethylacetamide, poly-n-vinylmethylpropionamide, poly-n-vinyl ethylpropionamide, poly-n-vinylmethylisobutyramide, poly-n-vinyl-2-pyrrolidone, poly-n-vinypiperidone also known as polyvinylpyrrolidone and as poly-n-vinylpyrroledone, poly-n-vinylcaprolactam, poly-n-vinyl-5-methyl-2-pyrrolidone and poly-n-vinyl-3-methyl-2-pyrrolidone, and poly-n-vinylpyrrolidone copolymer with a member selected from the group consisting of vinyl acetate, vinyl alcohol, vinyl chloride, vinyl fluoride, vinyl butyrate, vinyl laurate and vinyl stearate represented by small circles 19; and 0 wt %, where wt % is weight percent, 35 wt % of a maltodextrin polymer composition comprising the formula $(C_6H_{12}O_5)_n H_2O$ wherein n is 3 to 7,500 and the maltodextrin polymer comprises a 500 to 1,250,000 number average molecular weight represented by a small square 20; as member selected from the group consisting of 0 wt % to 40 wt % of poly(etheylen oxide) having a molecular weight of 100,000 to 600,000 grams per mole, represented by half-circles 20a. Composition 15 optionally comprises from 0 to 4.5 wt % of a lubricant represented by magnesium stearate, calcium stearate or stearic acid. The total weight of all ingredients in composition 15 is equal to 100 wt %, weight percent.

Compartment 14 comprises a displacement composition or push layer 21. Displacement composition 21 comprises a polymer member selected from the group consisting of a polymer possessing a repeating molecular unit $-(O-CH_2CH_2)_n$ wherein n is a positive whole number of 50,000 to 300,000 as represented by a poly(alkylene oxide) comprising poly(ethylene oxide) seen as wavy line 22; a maltodextrin polymer of the formula $(C_6H_{12}O_5)_n H_2O$ wherein n is 50 to 62,000 and comprises a 9,000 to 10,000,000 molecular weight and represented by triangle 23; a carboxymethylcellulose polymer comprising a 10,000 to 5,000,000 molecular weight represented by alkali carboxymethylcellulose, sodium carboxymethylcellulose and potassium carboxymethylcellulose, ammonium carboxymethylcellulose, sodium carboxymethyl-2-hydroxyethylcellulose, sodium carboxymethyl-methylcellulose, alkali carboxymethyl-hydroxypropyl-methylcellulose, alkali carboxymethyl-2-hydroxyethyl-methylcellulose, alkali carboxymethyl-2-hydroxybutylmethylcellulose, alkali carboxymethyl-2-hydroxyethyl-ethylcellulose and alkali carboxymethyl-2-hydroxypropylcellulose, where alkali is sodium and potassium and seen in drawing FIG. 2 as hexagonal 23a. The polymers in push layer 21 provide unforeseen operating advantages as the polymer maintains its chemical composition during operation as it imbibes an external aqueous fluid including biological fluid while simultaneously pushing the drug from the dosage form essentially-free of substantially mixing the drug composition with the push composition. The displacement composition 21 comprises optionally from 4 to 35 wt % of an osmotically active compound, also known as osmagent and represented by vertical line 24. Representative of osmotically effective compounds comprises salts, oxides, esters that exhibit imbibition properties, carbohydrates and acids including a member selected from the group consisting of magnesium sulfate, magnesium chloride, sodium chloride, lithium chloride, potassium chloride, potassium sulfate, sodium sulfate, sodium sulfite, lithium sulfate, ammonium chloride, potassium lactate, mannitol, urea, magnesium succinate, tartaric acid, raffinose, sorbitol, sucrose, fructose, and glucose. Displacement layer 21 optionally comprises 0.5 wt % to 30 wt % of a cellulose polymer 25 represented by the letter v. Representative of cellulose polymer 25 comprise a member selected from the group consisting of hydroxypropylcellulose, hydroxypropylmethylcellulose, hydroxypropylethylcellulose, hydroxypropylisopropylcellulose, hydroxypropylbutylcellulose, hydroxypropylpentylcellulose, and hydroxypropylhexylcellulose comprising a 9,000 to 225,000 molecular weight. The displacement composition optionally comprises 0 wt % to 5 wt % of lubricant stearic acid and, magnesium stearate, calcium oleate, oleic acid, and caprylic acid. The polymers are known in U.S. Pat. Nos. 3,845,770; and 4,160,020; in Handbook of Common Polymers by Scott, J. R., and Roff, W. J., published by CRC Press, Cleveland, Ohio.

Figure 3:
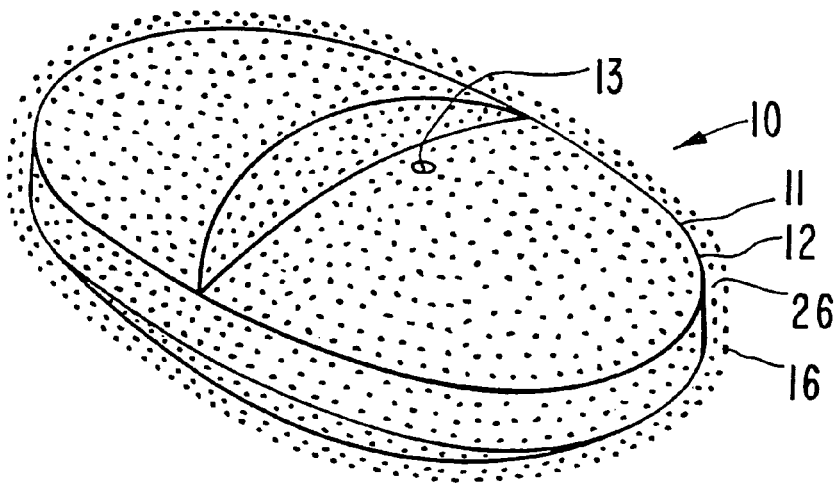
FIG. 3 is a view of a dosage form that depicts an external, instant-release of drug of the structural formula coated on the exterior surface of the dosage form.

Dosage form 10, as seen in drawing FIG. 3 depicts another preferred manufacture provided by the invention. Dosage form 10, in drawing FIG. 3, comprises an external coat on the exterior surface of dosage form 10. Coat 26 is a therapeutic composition comprising 10 mg to 150 mg of drug 16, represented by dots 16. Exterior coat 26 provides instant drug 16 for instant therapy. Drug 16 is blended with an aqueous-soluble composition comprising a carrier methylcellulose, hydroxypropylcellulose, hydroxypropylmethylcellulose, and blends of hydroxypropylcellulose and hydroxypropylmethylcellulose. Coat 26 optionally comprises polyethylene glycol or acetylated triglycerides. Coat 26 provides instant therapy as coat 26 dissolves or undergoes dissolution in the presence of a biological fluid and concurrently therewith delivers drug 16 to a drug receiving patient. Coat 26 provides instant therapy and it essentially overcomes the time required for the drug to be delivered from the dosage form.

Dosage form 10, as provided by this invention, and as seen in the above drawing figures can be manufactured for administering drug 16 by the oral route, and in another embodiment, dosage form 10 comprising exterior and interior drug 16 can be sized and shaped for administering drug 16 by the sublingual and buccal routes. The sublingual and buccal routes can be used for quicker therapy and they can be used when a smaller dose of drug 16 is needed for therapy. The buccal and sublingual routes can be used as a by-pass of the first pass of hepatic metabolism of drug 16. The sublingual or buccal routes can be used for administering the first dose of drug, followed by permitting dosage form 10 to enter the gastrointestinal tract for subsequent drug delivery.

Dosage form 10, when manufactured as an osmotic, controlled-release dosage form, comprises at least one passageway 13, or more than one passageway 13. The expression "at least one passageway" includes aperture, orifice, bore, pore, porous element through which the drug can be pumped, diffuse, travel or migrate, hollow fiber, capillary tube, porous overlay, porous insert, microporous member, porous composition, and the like. The expression also includes a material that erodes or is leached from wall 12 in the fluid environment of use to produce at least one passageway in dosage form 10. Representative material suitable for forming at least one passageway, or a multiplicity of passageways, includes an erodible poly(glycolic) acid or poly(lactic) acid member in the wall; a gelatinous filament; poly(vinyl alcohol); leachable materials such as fluid removable pore forming polysaccharides, salts, or oxides, and the like. A passageway or a plurality of passageways can be formed by leaching a material such as sorbitol, sucrose, lactose, fructose, or the like, from the wall to provide an osmotic dimensioned pore-passageway. The passageway can have any shape such as round, triangular, square, elliptical, and the like, for assisting in the metered release of drug from dosage form 10. Dosage form 10 can be constructed with one or passageways in spaced apart relation on one or more than a single surface of a dosage form. Passageways and equipment for forming passages are disclosed in U.S. Pat. Nos. 3,845,770 and 3,916,899 by Theeuwes and Higuchi; in U.S. Pat. No. 4,063,064 by Saunders et al; and in U.S. Pat. No. 4,088,864 by Theeuwes et al. Osmotic passageways comprising controlled-drug releasing dimension, sized, shaped and adapted as a drug releasing pore formed by aqueous leaching to provide a drug-releasing pore of controlled osmotic release rate are disclosed in U.S. Pat. No. 4,200,098 by Ayer and Theeuwes; and in U.S. Pat. No. 4,285,987 by Ayer and Theeuwes.

Wall 12 of osmotic dosage form 10 can be formed in one technique using the air suspension procedure. This procedure consists in suspending and tumbling the compressed drug-push core laminate in a current of air and wall forming composition until a wall is applied to the drug-push compartment. The air suspension procedure is well-suited for independently forming the wall. The air suspension procedure is described in U.S. Pat. No. 2,799,241; J. Am. Pharm. Assoc., Volume 48, pages 451 to 454, (1959); and ibid, Volume 49, pages 82 to 84, (196). Osmotic dosage forms can also be coated with a wall forming composition in a Wurster® air suspension coater, using methylene dichloride-methanol cosolvent, 80:20, wt:wt, an ethanol-water, or acetone-water cosolvent, 95:5 wt:wt using 2.5 to 4% solids. The Aeromatic® air suspension coater using a methylene dichloride-methanol cosolvent, 80:20 wt:wt, also can be used for applying the wall. Other wall forming techniques such as pan coating system, where wall forming compositions are deposited by successive spraying of the composition on the drug-push compartment, accompanied by tumbling in a rotating pan. Finally, the wall coated compartments are dried in a forced air over at 30° C. to 50° C. for up to a week to free dosage form 10 of solvent. Generally, the walls formed by these techniques have a thickness of 2 to 30 mils with a presently preferred thickness of 4 to 10 mils.

Dosage form 10 of the invention is manufactured by standard manufacturing techniques. For example, in one manufacture the beneficial drug and other ingredients comprising the drug layer facing the exit means are blended and pressed into a solid layer. The drug and other ingredients can be blended with a solvent and mixed into a solid or semisolid formed by conventional methods such as ball-milling, calendering, stirring or rollmilling and then pressed into a preselected shape. The layer possesses dimensions that correspond to the internal dimensions of the area the layer is to occupy in the dosage form and it also possesses dimensions corresponding to the second layer for forming a contacting arrangement therewith. Next, the push layer, is placed in contact with the drug layer. The push layer is manufactured using techniques for providing the drug layer. The layering of the drug layer and the push layer can be fabricated by conventional press-layering techniques. Finally, the two layer compartment forming members are surrounded and coated with an outer wall. A passageway is laser, leached, or mechanically drilled through the wall to contact the drug layer, with the dosage form optically oriented automatically by the laser equipment for forming the passageway on the preselected surface when a laser is used for forming the passageway.

In another manufacture, the dosage form is manufactured by the wet granulation technique. In the wet granulation technique, for example, the drug and the ingredients comprising the drug layer are blended using an organic solvent, such as isopropyl alcohol-ethylene dichloride 80:20 v:v (volume: volume) as the granulation fluid. Other granulating fluid such as denatured alcohol 100% can be used for this purpose. The ingredients forming the drug layer are individually passed through a 40 mesh screen and then thoroughly blended in a mixer. Next, other ingredients comprising the drug layer are dissolved in a portion of the granulation fluid, such as the cosolvent described above. Then the latter prepared wet blend is slowly added to the drug blend with continual mixing in the blender. The granulating fluid is added until a wet blend is produced, which wet mass then is forced through a 20 mesh screen onto oven trays. The blend is dried for 18 to 24 hours at 30° C. to 50° C. The dry granules are sized then with a 20 mesh screen. Next, a lubricant is passed through an 80 mesh screen and added to the dry screen granule blend. The granulation is put into milling jars and mixed on a jar mill for 1 to 15 minutes. The push layer is made by the same wet granulation techniques. The compositions are pressed into their individual layers in a Manesty® press-layer press.

Another manufacturing process that can be used for providing the compartment-forming composition layers comprises blending the powered ingredients for each layer independently in a fluid bed granulator. After the powered ingredients are dry blended in the granulator, a granulating fluid, for example, poly(vinyl-pyrrolidone) in water, or in denatured alcohol, or in 95:5 ethyl alcohol/water, or in blends of ethanol and water is sprayed onto the powders. Optionally, the ingredients can be dissolved or suspended in the granulating fluid. The coated powders are then dried in a granulator. This process granulates all the ingredients present therein while adding the granulating fluid. After the granules are dried, a lubricant such as stearic acid or magnesium stearate is added to the granulator. The granules for each separate layer are pressed then in the manner described above.

The dosage form of the invention is manufactured in another manufacture by mixing a drug with composition forming ingredients and pressing the composition into a solid lamina possessing dimensions that correspond to the internal dimensions of the compartment. In another manufacture the drug and other drug composition-forming ingredients and a solvent are mixed into a solid, or a semisolid, by conventional methods such as ballmilling, calendering, stirring or rollmilling, and then pressed into a preselected layer forming shape. Next, a layer of a composition comprising an osmopolymer and an optional osmagent are placed in contact with the layer comprising the drug. The layering of the first layer comprising the drug and the second layer comprising the osmopolymer and optional osmagent composition can be accomplished by using a conventional layer press technique. The wall can be applied by molding, spraying or dipping the pressed bilayer's shapes into wall forming materials. Another and presently preferred technique that can be used for applying the wall is the air suspension coating procedure. The procedure consists in suspending and tumbling the two layers in current of air until the wall forming composition surrounds the layers. The air suspension procedure is described in U.S. Pat. No. 2,799, 241; J. Am. Pharm. Assoc., Vol. 48 pp 451-454 (1979); and, ibid, Vol. 49, pp 82-84 (1960). Other standard manufacturing procedures are described in Modem Plastics Encyclopedia, Vol 46, pp 62-70 (1969); and in Pharmaceutical Science, by Remington, 14th Ed., pp 1626-1678 (1970), published by Mack Publishing Co., Easton, Pa.

Exemplary solvents suitable for manufacturing the wall, the laminates and laminae include inert inorganic and organic solvents final laminated wall. The solvents broadly include members selected for the group consisting of aqueous solvents, alcohols, ketones, esters, ethers, aliphatic hydrocarbons, halogenated solvents, cyclaliphatics, aromatics, heterocyclic solvents and mixtures thereof. Typical solvents include acetone, diacetone, alcohol, methanol, ethanol, isopropyl alcohol, butyl alcohol, methyl acetate, ethyl acetate, isopropyl acetate, n-butyl acetate, methyl isobutyl ketone, methyl propyl ketone, n-hexane, n-heptaene ethylene glycol monoethyl ether, ethylene glycol monoethyl acetate, methylene dichloride, ethylene dichloride, propylene dichloride, carbon tetrachloride, chloroform, nitroethane, nitropropane, tetrachoroethan, ethyl ether, isopropyl ether, cyclohexane, cyclooctane, benzene, toluene, naphtha, tetrahydrofuran, diglyme, aqueous and nonaqueous mixtures thereof, such as acetone and water, acetone and methanol, acetone and ethyl alcohol, methylene dichloride and methanol, and ethylene dichloride and methanol.

The following embodiments are also contemplated by the present invention:

(1) A therapeutic composition comprising 0.5 mg to 750 mg of a drug of the formula of drug 16, wherein the drug of the formula is blended with a poly(alkylene oxide) polymer.

(2) A therapeutic composition comprising 0.5 mg to 750 mg of a drug of the formula of drug 16, wherein the drug of the formula is blended with a cellulose polymer.

(3) A therapeutic composition comprising 0.5 mg to 750 mg of a drug of the formula of drug 16, wherein the drug of the formula is blended with a maltodextrin polymer.

(4) A method for administering a drug to the gastrointestinal tract of an animal, wherein the method comprises: (a) admitting orally into the animal a dosage form comprising a drug of the formula of 1-[2-(dimethylamino)-1-(4-methoxyphenyl)ethyl]-cyclohexanol which drug possesses antidepressant therapy and the dosage form comprises a member selected from the group consisting of a sustained-release dosage form and a controlled-release dosage form; and, (b) administering the drug from the dosage form over an extended period of time in a therapeutically responsive dose to produce the antidepressant therapy.

(5) A dosage form for administering a drug to an environment of use, wherein the dosage form comprises a drug of the formula of 1-[2-(dimethylamino)-1-(4-methoxyphenyl) ethyl]-cyclohexanol which dosage form comprises a member selected from the group consisting of a sustained-release dosage form and a controlled release dosage form, and wherein said dosage form comprises means for storing the drug and means for releasing the drug over an extended period of time.

(6) A dosage form for the oral delivery of a drug to an environment of use, wherein the dosage form comprises: (a) a wall comprising at least in part a composition permeable to the passage of fluid, which wall surrounds: (b) a compartment; (c) a drug composition in the compartment comprising a drug of the formula of drug 16; and (d) a displacement in the compartment comprising a composition comprising an osmotically active compound; and, (e) an exit passageway in the dosage form for delivering the drug composition from the dosage form.

(7) A dosage form for the oral delivery of the drug to an environment of use according to (6), wherein the drug is 1-[2-(dimethylamino)-1(4-methoxeyphenyl)ethyl]-cyclohexanol.

DETAILED DISCLOSURE OF EXAMPLES OF THE INVENTION

The following examples are merely illustrative of the present invention and they should not be considered as limiting the scope of the invention in any way as these examples and other equivalents thereof will become apparent to those versed in the art in the light of the present disclosure, the drawings and accompanying claims.

Example 1

A dosage form adapted for delivering a drug in a therapeutic range is manufactured as follows: first a displacement or push layer is prepared by blending and passing through a stainless steel sizing screen having a mesh opening of 420 microns 587.5 grams of sodium carboxymethylcellulose having a degree of polymerization of approximately 3,200 and a degree of substitution of 0.7 carboxymethyl groups per anhydroglucose unit, 300 grams of powdered sodium chloride, 50 grams of hydroxypropylcellulose having a molecular weight of approximately 60,000 grams per mole, and 50 grams of hydroxypropylmethylcellulose having an average methoxyl content of 29 weight percent and an average hydroxypropyl content of 10 weight percent and an average molecular weight of approximately 11,300 grams per mole. Next 10 grams of red ferric oxide were passed through a sizing screen having openings of approximately 250 microns. The resulting powders were mixed in a planetary mixer to a uniform blend. The resulting blend was wet granulated by adding with stirring anhydrous ethyl alcohol until, a cohesive mass was formed. This mass was passed through a sizing screen having openings of approximately 840 microns, forming coated displacement particles, which were an dried overnight at ambient temperature and humidity. The dried particles were then passed again through the 840 micron sizing screen. Next 2.5 grams of magnesium stearate, which had been previously sized through a mesh having 180 micron openings, were tumble mixed into the coated particles.

A composition comprising a drug of the structural formula was prepared as follows: first, a drug composition was prepared by passing 840 grams of venlafaxine hydrochloride, 100 grams of hydroxypropylcellulose having a molecular weight of approximately 60,000 grams per mole, and 50 grams of polyvinylpyrrolidone having a molecular weight of approximately 40,000 grams per mole, were passed through a sizing having openings of approximately 420 microns, and mixed in a planetary mixer to yield a uniform blend. Then, anhydrous ethyl alcohol was added to the mixture with stirring to produce a cohesive damp mass. The resulting damp mass was sized through a sieve having an opening of 840 microns, producing coated venlafaxine drug, which was air dried overnight. The resulting dried coated venlafaxine drug was passed again through the sizing screen having an 840 micron opening. Next, 10 grams of magnesium stearate, sized to 180 microns, was tumble mixed into the blend.

Next, the displacement-push composition and the drug composition were formed into a bilayer core as follows: first, 87 mg of the drug composition was placed in a 9/32 inch round die cavity and lightly tamped with a standard concave round tooling to form a slightly cohesive layer. Then, 70 mg of push composition was added to the die and the resulting fill was compressed with a final force of 2 tons, thereby forming a two layer cores.

The bilayer cores were placed next in a coating pan having a 12 inch diameter and they were coated with a wall-forming solution. The wall-forming solution was prepared by dissolving 380 grams of cellulose acetate having an acetyl content of 39.8 weight percent in 7,220 grams of acetone. In a separate mixing vessel, 20 grams of polyethylene glycol having a molecular weight of approximately 3,350 grams per mole were dissolved in approximately 380 grams of purified water. The two solutions were mixed to form the wall-coating solution which was spray coated onto the cores until about 20 mg of wall composition was deposited on the surfaces of the bilayer core.

A delivery exit port was formed across the wall by drilling an exit port, centered on the face of the dosage form on the drug composition side of the dosage form. The resulting dosage form was placed in simulated physiological fluid at 37° C., and the dosage form delivered a dose of 73 mg of venlafaxine hydrochloride at a controlled, zero rate over an extended duration of 15 hours.

Example 2

The procedure of Example 1 was followed with the manufacturing procedures as set forth, except that the drug composition comprises 890 grams of venlafaxine hydrochloride, 100 grams of hydroxypropylcellulose, and 10 grams of magnesium stearate. The resulting dosage form released in simulated intestinal fluid 77 mg of venlafaxine hydrochloride at a zero-order rate over an extended duration of 16 hours.

Example 3

The procedure of Example 1 was followed with all manufacturing steps as described, except that the drug composition consists of 650.0 grams of venlafaxine hydrochloride, 240.0 grams of maltodextrin having an average molecular weight of approximately 1800 grams per mole and an average degree of polymerization of 11.1, 80.0 grams of hydroxypropyl cellulose, 20.0 grams of polyvinyl pyrrolidone, and 10.0 grams of magnesium stearate. The resulting dosage form was tested in artificial intestinal fluid, the dosage form delivered a dose of 57 mg of venlafaxine hydrochloride at zero order rate over a period of 15 hours.

Example 4

The procedure of Example 1 was repeated with the manufacture as previously set-forth, except that the drug composition consists of 840.0 grams of venlafaxine hydrochloride, 150.0 grams of polyethylene oxide having an average molecular weight of approximately 100,000 grams per mole, and 10.0 grams of magnesium stearate. The wall weight weighed approximately 25 mg. The resulting dosage forms were tested in simulated intestinal fluid, and they released a dose of 73 mg of venlafaxine hydrochloride at controlled rate over an extended period of 20 hours.

Example 5

The compositions were manufactured as in Example 1. The process of manufacture was the same except that the push layer manufactured was prepared in a fluid bed aqueous-based granulation process. This was accomplished by sizing the sodium carboxymethyl cellulose, the sodium chloride, the hydroxypropyl cellulose, and red ferric oxide through a screen having openings of 420 microns. The resulting powders were charged into a fluid bed granulation column and binder solution consisting of the hydroxypropyl methylcellulose at a 5 percent solids concentration in water was sprayed on, thereby forming the granules for the push layer.

Example 6

The compositions and processes followed in this example were the same as in Example 1 except the push consisted of 740.0 grams polyethylene oxide with an average molecular weight of approximately 5 million grams per mole, 200.0 grams of sodium chloride, 50.0 grams of hydroxypropyl methyl cellulose having average molecular weight of approximately 11,300 per mole, 5.0 grams of red ferric oxide, and 5.0 grams of magnesium stearate.

DESCRIPTION OF METHOD OF PERFORMING THE INVENTION

Additional embodiments of the invention pertains to a method for delivering a drug embraced by the structural formula of this invention for its intended therapy. One embodiment pertains to a method for delivering a drug of the formula by administering a dosage form comprising 0.5 mg to 750 mg of the drug from a dosage form selected from sustained-release and controlled-release dosage forms in a therapeutically responsive dose over an extended period of time. Another embodiment of the invention pertains to a method for delivering a drug of the formula disclosed in this invention, to the gastrointestinal tract of a human in need of this therapy, wherein the method comprises the steps of: (A) admitting orally into the gastrointestinal tract of the human a dosage form comprising: (1) a non-toxic wall composition comprising means for imbibing an external aqueous fluid through the wall into the dosage form, which wall surrounds and defines; (2) an internal compartment; (3) a drug composition comprising a drug of the formula in the compartment comprising a dosage unit amount of said drug; (4) a push composition in the compartment for pushing the drug composition from the compartment; (5) at least one exit means in the wall for delivering the drug from the dosage form; (B) imbibing fluid through the wall into the compartment thereby causing the composition to form a deliverable dosage form and concomitantly causing the push composition to expand and push the drug composition through the exit means from the dosage form; and (C) deliver the therapeutic drug in a therapeutically effective amount at a controlled rate over an extended period of time to the patient in need of said therapy. The method also comprising dispensing a dose amount of said drug from an instant release exterior dosage amount of drug to the patient for providing instant anti-depressant therapy.

Inasmuch as the foregoing specification comprises preferred embodiments of the invention, it is understood that variations and modifications may be made herein, in accordance with the inventive principles disclosed, without departing from the scope of the invention.

We claim:

1. A dosage form having sustained-release or controlled-release properties for delivering 1-[2-(dimethylamino)-1-(4-methoxyphenyl)ethyl]-cyclohexanol from the dosage form over an extended period of time in a therapeutically responsive dose to produce antidepressant therapy, the dosage form comprising:

(a) a wall comprising at least in part a composition permeable to the passage of fluid, but not to 1-[2-(dimethylamino)-1-(4-methoxyphenyl)ethyl]-cyclohexanol, which wall surrounds;
(b) a compartment comprising a first layer and a second layer;
(c) a drug composition in the first layer of the compartment comprising 1-[2-(dimethylamino)-1-(4-methoxyphenyl)ethyl]-cyclohexanol and a hydroxypropylalkylcellulose wherein said alkyl is of 1 to 7 carbons or a hydroxyalkylcellulose wherein said alkyl is of 1 to 6 carbons;
(d) a displacement composition in the second layer of the compartment comprising an osmotically active compound; and
(e) an exit passageway in the dosage form for delivering the drug composition from the dosage form.

2. The dosage form of claim 1, wherein said dosage form comprises a hydroxypropylalkylcellulose wherein said alkyl is of 1 to 7 carbons.

3. The dosage form of claim 1, wherein said hydroxypropylalkylcellulose comprises hydroxypropylmethylcellulose.

4. The dosage form of claim 1, wherein said hydroxyalkylcellulose is hydroxypropylcellulose.

5. The dosage form of claim 1, wherein the drug composition weighs about 25% more than the displacement composition.

6. The dosage form of claim 1, further comprising an external coat on the exterior of the wall that provides instant release of a drug for instant therapy, comprising a drug composition comprising 1-[2-(dimethylamino)-1-(4-methoxyphenyl)ethyl]-cyclohexanol.

7. The dosage form of claim 1, wherein said extended period of time is at least 15 hours.

8. The dosage form of claim 1, wherein said extended period of time is at least 16 hours.

9. The dosage form of claim 1, wherein said extended period of time is at least 20 hours.

10. The dosage form of claim 1, wherein the osmotically active compound is selected from the group consisting of salts, oxides, esters, carbohydrates and acids.

11. The dosage form of claim 10 wherein said osmotically active compound is a salt selected from the group consisting of magnesium sulfate, magnesium chloride, sodium chloride, lithium chloride, potassium chloride, potassium sulfate, sodium sulfate, sodium sulfite, lithium sulfate, ammonium chloride, potassium lactate, magnesium succinate.

12. The dosage form of claim 11 wherein said salt is sodium chloride.

13. A dosage form having controlled-release properties for delivering 1-[2-(dimethylamino)-1-(4-methoxyphenyl)ethyl]-cyclohexanol from the dosage form over an extended period of time in a therapeutically responsive dose to produce antidepressant therapy, the dosage form comprising:
(a) a wall comprising at least in part a composition permeable to the passage of fluid, but not to 1-[2-(dimethylamino)-1-(4-methoxyphenyl)ethyl]-cyclohexanol, which wall surrounds;
(b) a compartment comprising a first layer and a second layer;
(c) a drug composition in the first layer of the compartment comprising 1-[2-(dimethylamino)-1-(4-methoxyphenyl)ethyl]-cyclohexanol and poly(ethylene oxide);
(d) a displacement composition in the second layer of the compartment comprising an osmotically active compound and poly(ethylene oxide); and
(e) an exit passageway in the dosage form for delivering the drug composition from the dosage form.

14. The dosage form of claim 13, further comprising an external coat on the exterior of the wall that provides instant release of a drug for instant therapy, comprising a drug composition comprising 1-[2-(dimethylamino)-1-(4-methoxyphenyl)ethyl]-cyclohexanol.

15. The dosage form of claim 13, wherein the osmotically active compound is selected from the group consisting of salts, oxides, esters, carbohydrates and acids.

16. The dosage form of claim 15 wherein said osmotically active compound is a salt selected from the group consisting of magnesium sulfate, magnesium chloride, sodium chloride, lithium chloride, potassium chloride, potassium sulfate, sodium sulfate, sodium sulfite, lithium sulfate, ammonium chloride, potassium lactate, magnesium succinate.

17. The dosage form of claim 16 wherein said salt is sodium chloride.

18. The dosage form of claim 13, wherein said extended period of time is at least 15 hours.

19. The dosage form of claim 13, wherein said extended period of time is at least 16 hours.

20. The dosage form of claim 13, wherein said extended period of time is at least 20 hours.

21. A dosage form having sustained-release or controlled-release properties for delivering 1-[2-(dimethylamino)-1-(4-methoxyphenyl)ethyl]-cyclohexanol from the dosage form over an extended period of time in a therapeutically responsive dose to produce antidepressant therapy, the dosage form comprising:
(a) a wall comprising at least in part a composition permeable to the passage of fluid, but not to 1-[2-(dimethylamino)-1-(4-methoxyphenyl)ethyl]-cyclohexanol, which wall surrounds;
(b) a compartment comprising a first layer and a second layer;
(c) a drug composition in the first layer of the compartment comprising 1-[2-(dimethylamino)-1-(4-methoxyphenyl)ethyl]-cyclohexanol and a hydroxyalkylcellulose wherein said alkyl is of 1 to 6 carbons;
(d) a displacement composition in the second layer of the compartment comprising an osmotically active compound; and
(e) an exit passageway in the dosage form for delivering the drug composition from the dosage form.

* * * * *